United States Patent
Wu et al.

(10) Patent No.: US 10,013,569 B2
(45) Date of Patent: Jul. 3, 2018

(54) PRIVACY-PRESERVING DATA COLLECTION, PUBLICATION, AND ANALYSIS

(71) Applicant: University of Florida Research Foundation, Incorporated, Gainesville, FL (US)

(72) Inventors: Samuel Shangwu Wu, Gainesville, FL (US); Shigang Chen, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 116 days.

(21) Appl. No.: 15/029,512

(22) PCT Filed: Oct. 15, 2014

(86) PCT No.: PCT/US2014/060715
§ 371 (c)(1),
(2) Date: Apr. 14, 2016

(87) PCT Pub. No.: WO2015/057854
PCT Pub. Date: Apr. 23, 2015

(65) Prior Publication Data
US 2016/0253514 A1   Sep. 1, 2016

Related U.S. Application Data

(60) Provisional application No. 61/891,106, filed on Oct. 15, 2013.

(51) Int. Cl.
*H04L 29/06* (2006.01)
*G06F 21/62* (2013.01)
(Continued)

(52) U.S. Cl.
CPC .......... *G06F 21/6218* (2013.01); *G06F 17/16* (2013.01); *G06F 17/18* (2013.01);
(Continued)

(58) Field of Classification Search
CPC .................................................. G06F 21/6218
See application file for complete search history.

(56) References Cited

U.S. PATENT DOCUMENTS

5,295,188 A * 3/1994 Wilson ................... H04L 9/302
235/379
8,055,668 B2 * 11/2011 Pomroy .............. G06F 21/6227
707/756
(Continued)

OTHER PUBLICATIONS

Hoffmann, Walter. "Iterative algorithms for Gram-Schmidt orthogonalization." Computing 41.4 (1989): 335-348, hereinafter "Hoffmann".*
(Continued)

*Primary Examiner* — Shawnchoy Rahman
(74) *Attorney, Agent, or Firm* — Alston & Bird LLP

(57) ABSTRACT

A data collection procedure is described, which can be performed automatically for each subject of a study as the participant produces the data being collected. In one case, the procedure transforms the data matrix X (of the participants' data) to AXB, where matrix A is a row operator that transforms data records (cases) in X and matrix B is a column operator that transforms data attributes (variables) in X, and the keys to generate these random operators are held separately by different parties. In another case, each participant's data is decomposed into a sum of k vectors before being collected and variously transformed by a plurality of masking service providers.

18 Claims, 18 Drawing Sheets

(51) Int. Cl.
*H04L 9/00* (2006.01)
*G06F 17/18* (2006.01)
*G06F 17/16* (2006.01)
*G16H 10/20* (2018.01)
*G16H 10/60* (2018.01)

(52) U.S. Cl.
CPC ......... *G06F 21/6245* (2013.01); *G16H 10/20* (2018.01); *G16H 10/60* (2018.01); *H04L 9/008* (2013.01); *H04L 2209/46* (2013.01)

(56) References Cited

U.S. PATENT DOCUMENTS

| | | |
|---|---|---|
| 2004/0258240 A1 | 12/2004 | Singh |
| 2006/0264714 A1 | 11/2006 | McGlennen et al. |
| 2008/0317173 A1* | 12/2008 | Kim .................... H04L 25/0204 375/341 |
| 2009/0010428 A1 | 1/2009 | Delgosha et al. |
| 2009/0204859 A1* | 8/2009 | Cousins .............. G06F 11/1004 714/701 |
| 2011/0164672 A1 | 7/2011 | Jiang et al. |
| 2012/0166809 A1 | 6/2012 | Barton et al. |

OTHER PUBLICATIONS

Mezzadri, Francesco. "How to generate random matrices from the classical compact groups." arXiv preprint math-ph/0609050 (2006).*

International Search Report/Written Opinion, International Application No. PCT/US2014/060715, PCT/ISA/210, PCT/ISA/237, dated Jan. 26, 2015.

* cited by examiner

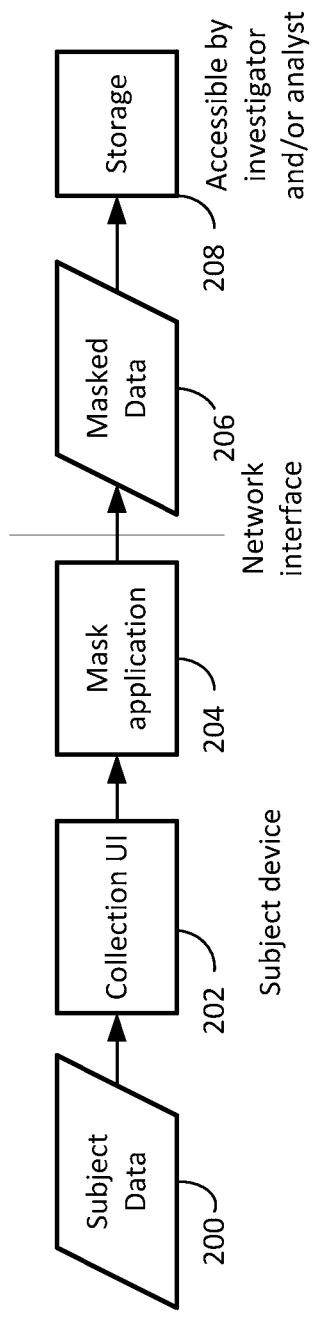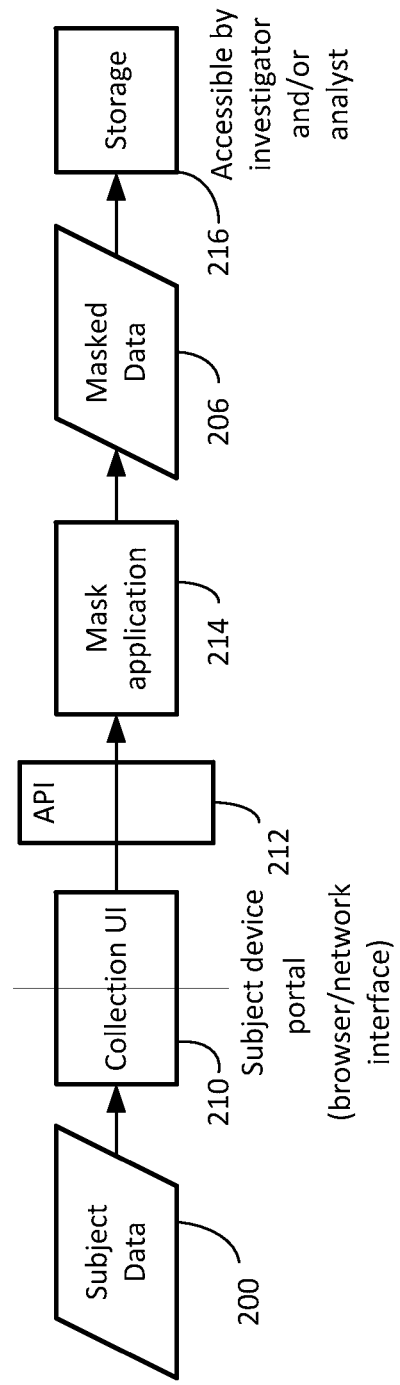

```
function M = GenerateROM(SeedValue, p)
rng(SeedValue);
Z1 = [ones(p, 1) randn(p, p-1)];
M1 = GramSchmidtOrthonorm(Z1);
rng(SeedValue+2);
Z2 = [ones(p, 1) randn(p, p-1)];
M2 = GramSchmidtOrthonorm(Z2);
M = M1 * M2';

function M = GramSchmidtOrthonorm(Z)
[p, col] = size(Z); Y = []; M = [];
for i = 1:p
    v = Z(:, i); u = v;
    for j = 1:(i-1)
        y = Y(:, j);
        u = u - (y' * v) / (y' *y) *y;
    end
    Y = [Y u];
    M = [M u/sqrt(u'*u)];
end;
```

FIG. 4

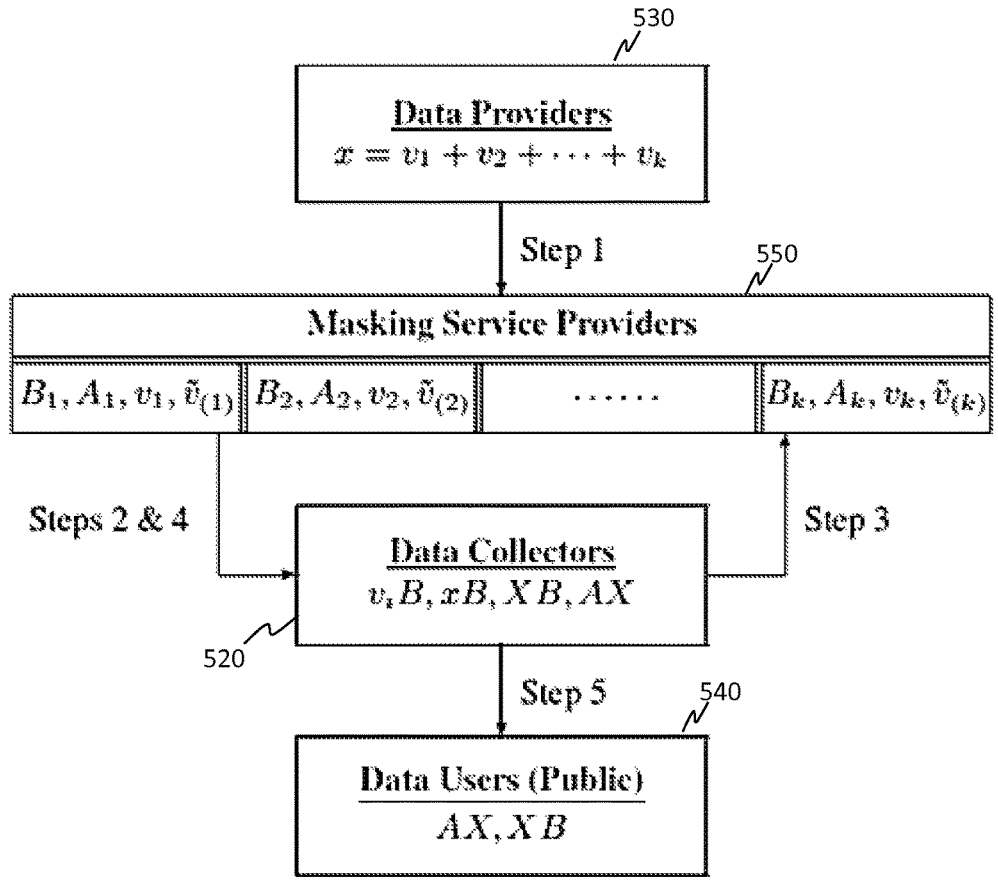

FIG. 5E

Table 1: Variables from the LEAPS study

| Variable | Description |
|---|---|
| Response | Improved functional level of walking 1 year after the stroke (Yes/No) |
| Δ | Change in walking speed from 2-month to 12-month post-stroke (meter/sec) |
| Group | Treatment group, 1 = Locomotor Training Program; 0 = Home Exercise Program |
| Age | Age at stroke onset (years) |
| BBS | Berg Balance Scale in sitting, standing, reaching, shifting weight, and turning |
| 2moWS | Comfortable walking speed from 10-meter walk test at 2-month baseline (m/s) |
| Steps | Total steps walked during a day |
| ADL-iADL | Activities of daily living (ADL's) and instrumental activities of daily life (iADL's) |

FIG. 6

Table 2: Random subset of 20 observations from LEAPS (X)

| ID | Response | Group | Δ | Age | BBS | 2moWS | Steps | ADL-iADL | QA |
|---|---|---|---|---|---|---|---|---|---|
| 1 | 0 | 1 | 0.08 | 63 | 30 | 0.09 | 1981 | 50 | 888 |
| 2 | 1 | 0 | 0.67 | 57 | 40 | 0.49 | 6017 | 62.5 | 888 |
| 3 | 1 | 0 | 0.20 | 47 | 43 | 0.44 | 5156 | 87.5 | 888 |
| 4 | 1 | 1 | 0.52 | 38 | 39 | 0.26 | 4193 | 80 | 888 |
| 5 | 1 | 1 | 0.47 | 83 | 36 | 0.77 | 4462 | 60 | 888 |
| 6 | 1 | 0 | 0.34 | 54 | 29 | 0.17 | 3706 | 80 | 888 |
| 7 | 0 | 1 | -0.07 | 50 | 13 | 0.13 | 3653 | 47.5 | 888 |
| 8 | 1 | 1 | 0.34 | 68 | 48 | 0.75 | 9234 | 72.5 | 888 |
| 9 | 1 | 0 | 0.25 | 57 | 47 | 0.46 | 6699 | 72.5 | 888 |
| 10 | 1 | 0 | 0.48 | 65 | 39 | 0.46 | 8687 | 47.5 | 888 |
| 11 | 1 | 1 | 0.15 | 43 | 9 | 0.08 | 382 | 50 | 888 |
| 12 | 1 | 0 | 0.12 | 81 | 40 | 0.34 | 408 | 67.5 | 888 |
| 13 | 0 | 1 | -0.13 | 76 | 48 | 0.53 | 786 | 32.5 | 888 |
| 14 | 1 | 1 | 0.15 | 84 | 29 | 0.51 | 2761 | 42.5 | 888 |
| 15 | 1 | 0 | 0.29 | 75 | 39 | 0.75 | 5742 | 85 | 888 |
| 16 | 1 | 1 | 0.20 | 65 | 33 | 0.35 | 2673 | 42.5 | 888 |
| 17 | 1 | 1 | 0.67 | 65 | 45 | 0.58 | 8493 | 75 | 888 |
| 18 | 1 | 1 | 0.15 | 66 | 24 | 0.22 | 3408 | 55 | 888 |
| 19 | 1 | 0 | 0.33 | 51 | 40 | 0.25 | 4780 | 50 | 888 |
| 20 | 1 | 1 | 0.22 | 90 | 44 | 0.54 | 2814 | 100 | 888 |

FIG. 7

Table 3: Attribute-transformed data $X_B$

| ID | Response | Group | Δ | Age | BBS | 2moWS | Steps | ADL/iADL | QA |
|---|---|---|---|---|---|---|---|---|---|
| 1 | 1489.67 | 1729.95 | 2010.32 | 930.02 | 964.79 | 996.87 | 2461.03 | 698.66 | 1151.80 |
| 2 | 2882.19 | 3454.09 | 4162.38 | 1948.20 | 1063.32 | 1655.42 | 5825.88 | 933.77 | 1851.03 |
| 3 | 2594.19 | 3104.83 | 3717.48 | 1731.65 | 1059.48 | 1516.79 | 5123.55 | 890.51 | 1695.35 |
| 4 | 2252.39 | 2689.30 | 3193.55 | 1482.39 | 1032.71 | 1352.64 | 4308.62 | 826.03 | 1517.52 |
| 5 | 2363.33 | 2795.10 | 3350.83 | 1569.81 | 1030.05 | 1417.52 | 4552.12 | 859.96 | 1605.54 |
| 6 | 2088.61 | 2481.92 | 2938.04 | 1363.11 | 1020.78 | 1281.37 | 3915.63 | 799.28 | 1442.36 |
| 7 | 2041.75 | 2433.38 | 2873.16 | 1334.17 | 995.48 | 1258.76 | 3837.81 | 767.73 | 1416.96 |
| 8 | 4003.63 | 4830.78 | 5887.13 | 2768.07 | 1143.95 | 2190.47 | 8520.84 | 1131.15 | 2423.78 |
| 9 | 3125.45 | 3751.89 | 4535.22 | 2124.20 | 1085.78 | 1769.91 | 6402.30 | 981.05 | 1973.58 |
| 10 | 3795.17 | 4578.49 | 5572.01 | 2620.09 | 1113.18 | 2090.19 | 8040.03 | 1081.23 | 2318.70 |
| 11 | 914.33 | 1044.79 | 1134.27 | 508.03 | 924.07 | 722.44 | 1114.09 | 579.58 | 842.54 |
| 12 | 977.15 | 1078.25 | 1208.16 | 552.63 | 944.79 | 757.66 | 1184.28 | 637.66 | 905.02 |
| 13 | 1092.35 | 1215.70 | 1388.04 | 643.01 | 932.02 | 806.19 | 1463.51 | 649.82 | 968.34 |
| 14 | 1767.46 | 2059.25 | 2432.83 | 1136.50 | 979.87 | 1134.59 | 3121.80 | 753.09 | 1306.61 |
| 15 | 2810.14 | 3354.89 | 4042.14 | 1891.81 | 1073.06 | 1628.40 | 5632.02 | 936.72 | 1821.86 |
| 16 | 1727.18 | 2020.19 | 2376.65 | 1106.06 | 976.74 | 1108.98 | 3032.98 | 739.63 | 1275.11 |
| 17 | 3746.71 | 4516.82 | 5491.97 | 2579.40 | 1128.47 | 2068.72 | 7904.03 | 1086.46 | 2291.22 |
| 18 | 1979.83 | 2339.25 | 2767.95 | 1288.68 | 999.24 | 1232.38 | 3655.67 | 777.69 | 1398.16 |
| 19 | 2447.83 | 2919.22 | 3494.24 | 1631.88 | 1027.17 | 1445.96 | 4780.57 | 856.20 | 1630.10 |
| 20 | 1827.35 | 2125.00 | 2513.70 | 1169.64 | 1021.13 | 1166.51 | 3222.82 | 793.45 | 1334.86 |

FIG. 8

Table 4: The doubly masked data transmitted to the data collectors $A\times B$

| ID | Response | Group | A | Age | BBS | 2moWS | Steps | ADL/iADL | QA |
|---|---|---|---|---|---|---|---|---|---|
| 1 | 1609.54 | 1895.61 | 2203.97 | 1016.95 | 972.04 | 1051.59 | 2778.59 | 704.19 | 1198.98 |
| 2 | 2986.11 | 3576.64 | 4316.75 | 2019.46 | 1087.68 | 1706.62 | 6054.20 | 967.05 | 1904.35 |
| 3 | 2022.75 | 2406.64 | 2842.71 | 1321.35 | 993.71 | 1249.68 | 3786.80 | 767.92 | 1410.01 |
| 4 | 1380.26 | 1602.95 | 1846.38 | 851.59 | 949.49 | 944.62 | 2217.48 | 667.80 | 1092.43 |
| 5 | 2938.08 | 3519.94 | 4241.92 | 1982.87 | 1088.62 | 1682.05 | 5934.72 | 960.19 | 1875.43 |
| 6 | 1844.14 | 2178.86 | 2563.22 | 1188.33 | 992.17 | 1162.35 | 3329.71 | 753.00 | 1321.26 |
| 7 | 2188.86 | 2593.58 | 3088.03 | 1438.44 | 1023.12 | 1327.94 | 4139.54 | 823.89 | 1502.21 |
| 8 | 3063.18 | 3669.71 | 4436.82 | 2078.82 | 1081.59 | 1740.28 | 6242.91 | 975.14 | 1945.83 |
| 9 | 1383.06 | 1601.86 | 1845.74 | 848.27 | 968.99 | 944.76 | 2196.86 | 686.08 | 1091.69 |
| 10 | 2433.49 | 2875.12 | 3451.93 | 1617.11 | 1050.00 | 1456.58 | 4705.00 | 884.99 | 1644.77 |
| 11 | 4235.89 | 5123.52 | 6253.54 | 2944.50 | 1136.59 | 2299.55 | 9111.94 | 1150.18 | 2542.64 |
| 12 | 1482.58 | 1698.19 | 1987.64 | 926.01 | 969.51 | 999.15 | 2409.40 | 719.42 | 1166.92 |
| 13 | 3561.00 | 4277.32 | 5202.38 | 2446.72 | 1107.73 | 1980.16 | 7445.52 | 1058.88 | 2206.53 |
| 14 | 2636.25 | 3141.59 | 3774.65 | 1766.32 | 1055.18 | 1547.25 | 5221.50 | 901.38 | 1734.88 |
| 15 | 2427.25 | 2911.24 | 3466.05 | 1611.41 | 1039.78 | 1442.17 | 4756.59 | 843.86 | 1606.54 |
| 16 | 335.77 | 286.99 | 220.27 | 86.60 | 889.38 | 451.26 | -356.43 | 521.62 | 581.71 |
| 17 | 2243.07 | 2665.21 | 3179.18 | 1485.15 | 1003.90 | 1347.89 | 4290.84 | 816.96 | 1529.16 |
| 18 | 3127.83 | 3748.10 | 4535.41 | 2126.57 | 1086.17 | 1772.60 | 6398.59 | 986.80 | 1980.37 |
| 19 | 2595.03 | 3111.69 | 3721.60 | 1733.20 | 1055.90 | 1520.32 | 5143.33 | 881.80 | 1694.27 |
| 20 | 1432.53 | 1638.32 | 1911.86 | 889.69 | 964.53 | 974.98 | 2292.44 | 708.50 | 1140.46 |

FIG. 9

Table 5: The matrix-masked data released to data users CAX

| ID | Response | Group | Δ | Age | BBS | 2moWS | Steps | ADL/iADL | QA |
|---|---|---|---|---|---|---|---|---|---|
| 1 | 0.82 | 0.75 | 0.09 | 60.91 | 33.20 | 0.13 | 633.67 | 67.76 | 888 |
| 2 | 0.31 | 1.43 | 0.07 | 84.76 | 39.35 | 0.67 | 2992.56 | 50.69 | 888 |
| 3 | 1.34 | 0.27 | 0.29 | 108.09 | 43.04 | 0.87 | 5316.90 | 81.61 | 888 |
| 4 | 0.50 | 0.93 | 0.30 | 68.94 | 17.70 | 0.35 | 3916.80 | 28.43 | 888 |
| 5 | 0.49 | 1.23 | 0.14 | 80.43 | 49.46 | 0.51 | 2537.80 | 89.87 | 888 |
| 6 | 0.31 | 0.81 | 0.07 | 47.74 | 23.39 | 0.01 | 3387.97 | 50.08 | 888 |
| 7 | 0.61 | -0.15 | 0.27 | 68.08 | 52.09 | 0.40 | 7100.86 | 51.89 | 888 |
| 8 | 1.36 | 0.39 | 0.72 | 47.80 | 47.55 | 0.56 | 8633.75 | 98.78 | 888 |
| 9 | 1.49 | -0.06 | 0.46 | 48.19 | 31.22 | 0.42 | 6596.91 | 90.43 | 888 |
| 10 | 0.28 | -0.20 | 0.05 | 52.30 | 33.94 | 0.34 | 1616.99 | 64.95 | 888 |
| 11 | 0.82 | 0.91 | -0.24 | 63.64 | 15.00 | 0.04 | -334.34 | 50.64 | 888 |
| 12 | 1.14 | 0.03 | 0.41 | 68.22 | 54.36 | 0.56 | 6267.50 | 45.89 | 888 |
| 13 | 1.05 | 0.85 | 0.14 | 60.35 | 42.17 | 0.70 | 5641.36 | 53.95 | 888 |
| 14 | 1.30 | 0.64 | 0.56 | 65.24 | 31.98 | 0.29 | 2323.23 | 70.15 | 888 |
| 15 | 0.73 | 0.99 | 0.45 | 58.41 | 36.90 | 0.55 | 10226.13 | 75.78 | 888 |
| 16 | 1.12 | 0.74 | 0.47 | 68.55 | 36.60 | 0.45 | 3782.03 | 57.37 | 888 |
| 17 | 0.94 | -0.22 | 0.29 | 59.64 | 35.54 | 0.38 | 4365.84 | 76.90 | 888 |
| 18 | 0.80 | 0.54 | 0.25 | 54.06 | 35.94 | 0.29 | 4149.46 | 59.08 | 888 |
| 19 | 0.78 | 1.13 | 0.28 | 61.54 | 34.54 | 0.43 | 2288.49 | 46.80 | 888 |
| 20 | 0.81 | 0.97 | 0.35 | 51.12 | 21.03 | 0.23 | 4591.08 | 48.95 | 888 |

FIG. 10

Table 6: Two selected records of augmented data ($x^*$)

| ID | Response | Group | Δ | Age | BBS | 2moWS | Steps | ADL/iADL |
|---|---|---|---|---|---|---|---|---|
| 1 | 0 | 1 | 0.08 | 63.00 | 30.00 | 0.09 | 1981.00 | 50.00 |
| 1 | 0 | 1 | -0.73 | -0.65 | -1.52 | 0.10 | 0.17 | 0.18 |
| 1 | 0 | 1 | 0.43 | -0.07 | -1.34 | -0.97 | 0.18 | -0.07 |
| 1 | 0 | 1 | -0.65 | 0.42 | -0.20 | 1.84 | 0.96 | 0.44 |
| 1 | 0 | 1 | 0.30 | 0.13 | -0.41 | 0.52 | 0.33 | -0.37 |
| 1 | 0 | 1 | 0.56 | 0.26 | 0.63 | 0.49 | 0.02 | -1.15 |
| 1 | 0 | 1 | -0.23 | -0.59 | 0.94 | 0.11 | 0.33 | -0.14 |
| 1 | 0 | 1 | 777 | 777 | 777 | 777 | 777 | 777 |
| 11 | 1 | 1 | 0.15 | 43.00 | 9.00 | 0.08 | 382.00 | 50.00 |
| 11 | 1 | 1 | -1.25 | 1.23 | 0.67 | -0.15 | -0.44 | -0.03 |
| 11 | 1 | 1 | -1.30 | 0.24 | -1.76 | 1.70 | -0.96 | 2.31 |
| 11 | 1 | 1 | -0.35 | 0.49 | 1.14 | 0.70 | -0.01 | -1.10 |
| 11 | 1 | 1 | -0.60 | 1.11 | 2.32 | 0.59 | 0.48 | 1.49 |
| 11 | 1 | 1 | 0.28 | 0.23 | -0.36 | 0.85 | 1.33 | 0.94 |
| 11 | 1 | 1 | -0.50 | -0.03 | -1.16 | 1.55 | 0.79 | -0.36 |
| 11 | 1 | 1 | 888 | 888 | 888 | 888 | 888 | 888 |

FIG. 12

Table 7: The first masked data for the two selected records $A_{x^*}$

| ID | Response | Group | Δ | Age | BBS | 2moWS | Steps | ADL | ADL/iADL |
|---|---|---|---|---|---|---|---|---|---|
| 1 | 0 | 1 | 270.41 | 293.10 | 279.91 | 271.78 | 989.49 | 288.78 |
| 1 | 0 | 1 | 645.01 | 692.09 | 665.50 | 645.81 | 2125.89 | 682.30 |
| 1 | 0 | 1 | 44.16 | 55.16 | 48.16 | 46.36 | 369.96 | 53.48 |
| 1 | 0 | 1 | 487.56 | 529.97 | 507.47 | 489.25 | 1813.87 | 520.40 |
| 1 | 0 | 1 | 647.02 | 688.57 | 665.46 | 647.18 | 1969.52 | 678.50 |
| 1 | 0 | 1 | 689.58 | 717.24 | 701.99 | 691.01 | 1561.07 | 711.46 |
| 1 | 0 | 1 | 624.98 | 646.12 | 634.50 | 626.04 | 1305.49 | 641.17 |
| 1 | 0 | 1 | 754.69 | 784.73 | 768.37 | 755.48 | 1708.41 | 777.74 |
| 111 | 1 | 1 | 306.89 | 327.30 | 313.44 | 312.49 | 447.92 | 329.55 |
| 111 | 1 | 1 | 735.15 | 770.95 | 743.79 | 739.88 | 1022.09 | 776.73 |
| 111 | 1 | 1 | 49.45 | 59.84 | 53.51 | 53.24 | 113.23 | 59.90 |
| 111 | 1 | 1 | 556.56 | 587.14 | 564.45 | 558.90 | 813.78 | 591.36 |
| 111 | 1 | 1 | 736.96 | 768.79 | 744.09 | 742.33 | 994.43 | 775.31 |
| 111 | 1 | 1 | 786.19 | 808.77 | 792.95 | 791.52 | 956.38 | 811.97 |
| 111 | 1 | 1 | 711.87 | 730.78 | 716.97 | 718.27 | 846.24 | 733.77 |
| 111 | 1 | 1 | 860.85 | 884.28 | 865.77 | 865.34 | 1046.93 | 888.19 |

FIG. 13

Table 8: The doubly masked data transmitted to the data collectors $Ax^*B$

| ID | Response | Group | $\Delta$ | Age | BBS | 2moWS | Steps | ADL/iADL |
|---|---|---|---|---|---|---|---|---|
| 1 | 0 | 1 | 512.06 | 670.18 | 518.28 | 509.62 | 333.79 | -150.46 |
| 1 | 0 | 1 | 1142.68 | 1466.70 | 1156.86 | 1137.88 | 774.90 | -222.41 |
| 1 | 0 | 1 | 154.30 | 226.60 | 156.15 | 152.18 | 73.37 | -145.31 |
| 1 | 0 | 1 | 934.21 | 1222.83 | 945.83 | 929.35 | 605.40 | -289.09 |
| 1 | 0 | 1 | 1090.71 | 1379.79 | 1104.07 | 1087.01 | 763.65 | -128.97 |
| 1 | 0 | 1 | 982.81 | 1173.33 | 990.32 | 979.73 | 766.78 | 179.38 |
| 1 | 0 | 1 | 853.43 | 1002.43 | 859.51 | 851.45 | 685.59 | 225.90 |
| 1 | 0 | 1 | 1075.13 | 1283.34 | 1084.04 | 1072.18 | 839.17 | 195.55 |
| 111 | 1 | 1 | 368.07 | 393.26 | 364.61 | 352.68 | 316.64 | 242.33 |
| 111 | 1 | 1 | 852.86 | 908.49 | 851.39 | 828.36 | 750.57 | 596.93 |
| 111 | 1 | 1 | 78.31 | 88.61 | 75.87 | 70.00 | 55.16 | 21.22 |
| 111 | 1 | 1 | 660.59 | 709.98 | 660.66 | 640.42 | 570.31 | 430.23 |
| 111 | 1 | 1 | 842.74 | 893.72 | 840.42 | 820.68 | 750.66 | 613.70 |
| 111 | 1 | 1 | 858.10 | 889.70 | 854.99 | 841.65 | 797.14 | 706.20 |
| 111 | 1 | 1 | 769.72 | 795.37 | 765.83 | 755.25 | 721.19 | 650.54 |
| 111 | 1 | 1 | 937.27 | 974.44 | 935.59 | 920.84 | 871.37 | 771.82 |

FIG. 14

Table 9: The matrix-masked data released to data users $XBC$

| ID | Response | Group | $\Delta$ | Age | BBS | 2moWS | Steps | ADL/iADL |
|----|----------|-------|----------|---------|---------|--------|--------|----------|
| 1  | 0        | 1     | -763.55  | 1565.76 | -202.63 | 499.48 | 713.98 | 311.14   |
|    | 1        | 1     | 888      | 888     | 888     | 888    | 888    | 888      |
| 11 | 1        | 1     | 888      | 888     | 888     | 888    | 888    | 888      |

FIG. 15

Table 10. Correspondence between two forms of counts in 2x2 table

| | Usual | | | | Vector | | |
|---|---|---|---|---|---|---|---|
| | $x_2 = 0$ | $x_2 = 1$ | Totals | | $x_2 = 0$ | $x_2 = 1$ | Totals |
| $x_1 = 0$ | $a$ | $b$ | $a+b$ | | — | — | — |
| $x_1 = 1$ | $c$ | $d$ | $c+d$ | | $x'_1 x_2$ | $x'_1 x_2$ | $x'_1 x_1$ |
| Totals | $a+c$ | $b+d$ | $n$ | | — | $x'_2 x_2$ | $n$ |

FIG. 16

PRIVACY-PRESERVING DATA COLLECTION, PUBLICATION, AND ANALYSIS

CROSS-REFERENCE TO RELATED APPLICATIONS

This application is the U.S. national stage application of International Patent Application No. PCT/US2014/060715, filed Oct. 15, 2014, which claims the benefit of U.S. Provisional Patent Application No. 61/891,106, filed Oct. 15, 2013, the disclosures of each of which are incorporated herein by reference in their entirety, including any figures, tables, and drawings.

GOVERNMENT FUNDING

This invention was made with government support under grant number GM118737, awarded by the National Institutes of Health. The government has certain rights in the invention.

BACKGROUND

A major obstacle that hinders medical and social research is the lack of data availability due to privacy concerns. A lack of procedures for protecting confidentiality still precludes data collection. This contributes to the lack of trust by potential subjects for providing confidential information.

For example, some people refuse to participate in research because they do not have enough trust in the confidentiality protection or are reluctant to confide secrets to strangers. In some cases, people may consent to research but purposely provide wrong information for those same reasons. The resulting error (or bias) in medical and social research from including the purposeful and intentional wrong information provided by a subject is referred to as evasive answer bias. Refusal bias may arise where a population of interest refuses to participate in the research, resulting in research not relevant to that population or skewed to the population of responders. In both cases (evasive answer bias and refusal bias), the results of medical and social research can be difficult to interpret and apply.

Even when people agree to participate and provide truthful confidential information, protecting confidentiality remains a challenging issue (American Association of Medical Colleges, 2010). The Health Insurance Portability and Accountability Act of 1996 (HIPAA) and subsequent rulings have spurred the implementation of a number of privacy protection procedures limiting access to confidential information. One of such procedures involves a review by an Institutional Review Board (IRB) that must approve release of medical records from a hospital. To facilitate data sharing, a number of technologies have been developed for masking data at the time of release. However, the current data masking approaches do not yet justify bypassing the bureaucratic IRB process because the private information is collected and accessed by investigators before the data masking occurs (and therefore requires the attention and review by the IRB). The IRB review process can take a significant amount of time and even when the IRB approves the release of data, the use of this data is subject to stringent restrictions.

BRIEF SUMMARY

Techniques and systems are described for preserving privacy of a subject's information at the time of collection while enabling relevant statistical analysis.

Masking procedures described herein can be performed at the time of data collection. Instead of masking data from a central repository after collection, masking can be performed in a distributed way at each participant's data-generating device: one subject or case (i.e., one row of a data matrix X) at a time, providing flexibility for incremental data collection and processing.

According to one embodiment, triple matrix masking can be performed using two row operators A and C that are orthogonal matrices and a column operator B that is a general invertible matrix. The procedure transforms a data matrix X to XB at initial capture (e.g., matrix B is a column operator that transforms data attributes (variables) in X). Then, a trusted party transforms XB to AXB, where matrix A is a row operator that transforms data records (cases) in X. A third transformation can be carried out by data collectors (or another party) to present the data to the public, for example by removing B from the doubly masked data and publishing CAX.

In another embodiment, the original data from each participant may be decomposed into a sum of k vectors. These components of the original data are individually transformed by being multiplied by a corresponding invertible matrix. The corresponding invertible matrices may be applied by associated masking parties. Then, the masked components may be aggregated into xB for each subject (e.g., row of a data matrix X) and the individual data xB can be aggregated into XB. The use of multiple masking parties providing associated matrices A and/or B further reduce likelihood of collusion.

In some implementations, a service or system may facilitate the triple matrix masking by providing access to the features and functionality that generates orthogonal and/or invertible matrices and performs data transformations as described herein. Various parties may access such features and functionality through authenticated portals.

The masked data maintains usefulness because statistical inference on parameters of interest can be conducted with the same results on the orthogonally transformed data as would have been available on the original data under the general linear model and the chi-squared test. The keys to generate the random matrices (A, B and C) are held separately. For example, for the triple matrix masking procedure described above, the key to generate A can be considered to be held by a trusted party and keys for B and C can be known to (or generated by) the data collectors (or another party). The actual data can be maintained entirely in confidence starting from the very moment when data is produced. Consequently, researchers and data analysts (and even the public) work only with masked data and do not see the original data. By avoiding contact with the original data from the beginning of the research process, the confidentiality of data can be protected and it may be possible to simplify the IRB approval process because no identifiable data is used.

In certain implementations, an error checking mechanism is built into the data collection process in order to make sure that the masked data used for analysis are indeed an orthogonal transformation of the original data. Partial masking can also be enabled to grant investigators the access to non-sensitive patient information while sensitive personal information remains hidden. In addition, the original data may be either record-transformed or attributed-transformed in support of different types of analysis.

This Summary is provided to introduce a selection of concepts in a simplified form that are further described below in the Detailed Description. This Summary is not

BRIEF DESCRIPTION OF THE DRAWINGS

FIGS. 2A and 2B illustrate system process flows for certain implementations.

FIG. 4 shows a program for generating a random orthogonal matrix according to one implementation.

FIG. 5E shows a diagram indicating each entity's knowledge about data for an implementation with a masking service provider.

FIG. 6 shows a Table of 8 variables used for an illustrative example of the matrix masking technique.

FIG. 7 shows Table 2 representing original data X, a random subset of 20 observations from LEAPS.

FIGS. 8-10 show Tables 3-5, illustrating matrix masked data for different entities according to an example implementation.

FIG. 11A is the actual data and its model fit and FIG. 11B is the masked data and its model fit.

FIGS. 12-15 show Tables 6-9, illustrating augmented matrix masked data for different entities according to an example implementation.

FIG. 16 shows Table 10, a 2×2 table of count data.

DETAILED DESCRIPTION

Techniques are described for preserving privacy of a subject's information at the time of collection while enabling relevant statistical analysis. Techniques are presented that inhibit investigators (as well as anyone except for participants themselves) from knowing the raw data pertaining to sensitive information. This technique may be referred to as a matrix masking technique, and in some cases may involve triple matrix masking. In addition to orthogonally transforming data, the subject techniques can be performed distributively at each participant's data generating device, allowing the data to be incrementally masked for each participant.

In some implementations, a service or system may facilitate the described matrix masking techniques. Various parties may access such features and functionality through authenticated portals. Authentication may be carried out through any suitable authentication methodology.

In one embodiment, a data matrix X (of the participant/subjects' data) is transformed to AXB, where matrix A is a row operator that transforms data records (cases) in X and matrix B is a column operator that transforms data attributes (variables) in X. The keys to generate these random operators can be held separately by an investigative team and a data collector or statistical team of analysts. According to certain implementations, no one but the participant/subject knows the original data X (particularly individual data x), but the same statistical inference on parameters of interest can be conducted for orthogonally transformed data as for the original data, with the use of the general linear model and the chi-squared test. In further embodiments, serial locks and quality assurance techniques are built in the data collection procedure to further improve the protection of data confidentiality and the reliability of the system.

According to an embodiment, matrix masking is performed to hide the original data from everyone, without loss of statistical utility. Transformations can be used starting at the time of data collection, so that the original data are masked from all investigators and analysts, while statistical analysis can still be performed with the same results from the masked data as if they were from the original data. This process can be used in any application that involves sensitive personal information.

Figure 1:
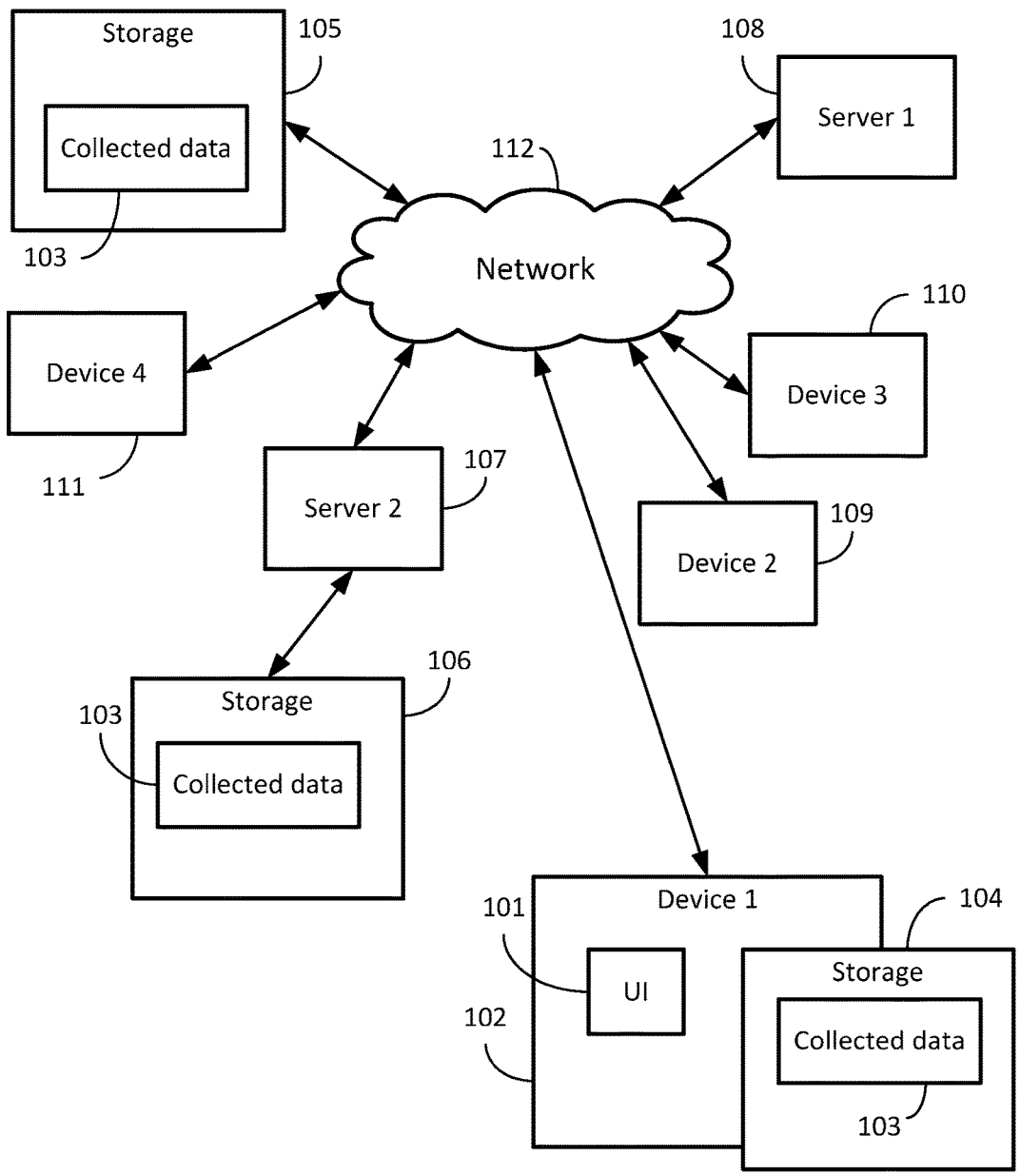
FIG. 1 illustrates an operating environment in which certain embodiments of the invention may be carried out.

FIG. 1 illustrates an operating environment in which certain embodiments of the invention may be carried out. Personal data of a subject may be entered via a user interface 101 of a program running on a first computing device 102.

In some cases, the program may be a local application. Data may be collected and stored as collected data 103 locally at the first computing device 102 in storage 104. The collected data 103 can be stored in a masked form. That is, as the data is collected via the user interface 101, matrix masking is performed to transform the data before storing as collected data 103 in storage 104. The collected data 103 may be shared for use and analysis by other researchers, investigators, or analysts. In some cases, the collected data 103 can be provided to a central repository in the form of cloud storage 105 or available as storage 106 accessed via a server or computing device 107 of a data management center, for example operated by a hospital or University. A system process flow may be implemented, for example, as illustrated in FIG. 2A. Referring to FIG. 2A, a subject's data 200 can be collected via a collection user interface 202 of a mask application 204 running on a subject's device. In some cases, sensitive information may be attached to the data from a sensor or monitor coupled to the device. The masked data 206 can be sent to storage 208 that is accessible by an investigator and/or analyst via a network interface.

In some cases, the user interface 101 may be rendered in a web browser providing a portal to a server 108 running an application for collecting a subject's information. The collected data 103 may be stored locally at the computing device 102, in a storage (not shown) associated with the server 108, in a central repository 105, and/or storage 106 accessed via a server or computing device 107 of a data management center. Server 108 may be one or more servers (or other computing devices) on which a service for facilitating data collection and/or matrix masking is embodied.

A system process flow may be implemented, for example, as illustrated in FIG. 2B. Referring to FIG. 2B, the subject's data 200 can be collected via a collection user interface 210 rendered in a browser of a subject's device. The user interface 210 can be associated with a mask application 214 running on a server (and which may be accessible by a subject device via an application programming interface 212 for a service providing the mask application 214). The masked data 206 generated by the mask application 214 can be stored in a storage 216 associated with the service providing the mask application 214 or another server/service. In some cases, sensitive information may be attached to the data from a sensor or monitor coupled to the device and this sensitive information is transformed using the mask application 214 along with data entered through the user interface 210.

The mask application(s) can be stored locally at a subject's device or stored remotely and/or distributed across multiple devices.

Returning to FIG. 1, the collected data 103 may be collected from and/or accessed by a number of parties via computing devices such as the second computing device 109, third computing device 109, and fourth computing device 109. In some implementations, the parties can include the data management center, data analyst(s), investigator(s), and the subject/participant. Data may be collected distributively and stored in a masked form as the data is collected.

Communication between devices can be carried out over a network 112. The network 112 can include, but is not limited to, an internet, an intranet, or an extranet, and can be any suitable communications network including, but not limited to, a cellular (e.g., wireless phone) network, the Internet, a local area network (LAN), a wide area network (WAN), a WiFi network, an ad hoc network or a combination thereof. Such networks may involve connections of network elements, such as hubs, bridges, routers, switches, servers, and gateways. The network may include one or more connected networks (e.g., a multi-network environment) including public networks, such as the Internet, and/or private networks such as a secure enterprise private network. Access to the network may be provided via one or more wired or wireless access networks as will be understood by those skilled in the art.

The computing devices and/or servers (e.g., devices 102, 107, 109, 110, and 111) may be embodied as a server, a desktop, laptop, smartphone, portable digital assistant (PDA), tablet, reader, game console, smart television and the like. In some cases, the computing devices can include monitors or medical equipment sensing or monitoring physiological or other changes and behaviors of a subject.

For example, in the context of stroke rehabilitation research, patient movement and activities can be continuously monitored and analyzed. These data can be used to construct an accurate measure of daily living, an objective version of the usual "Activities of Daily Living" variable. One such system consists of an ankle accelerometer and smartphone, with the smartphone programmed to continuously compute and transmit positions and activity variables to a clinic. The smartphone's geographical positioning system (GPS) may be used to provide location information for the patient. Because this data gives detailed information about patient locations at all times, many subjects are likely to refuse to participate in research due to concern about privacy. In order to include these privacy sensitive patients, the program running on the smartphone can mask the location information, but keeps information which is useful for statistical analysis.

According to certain embodiments of the invention, masking of data can be accomplished for each item or specific items of information input to a collection program. The masking can be accomplished through applying a masking technique that can ultimately include triple matrix masking.

Figure 3A:
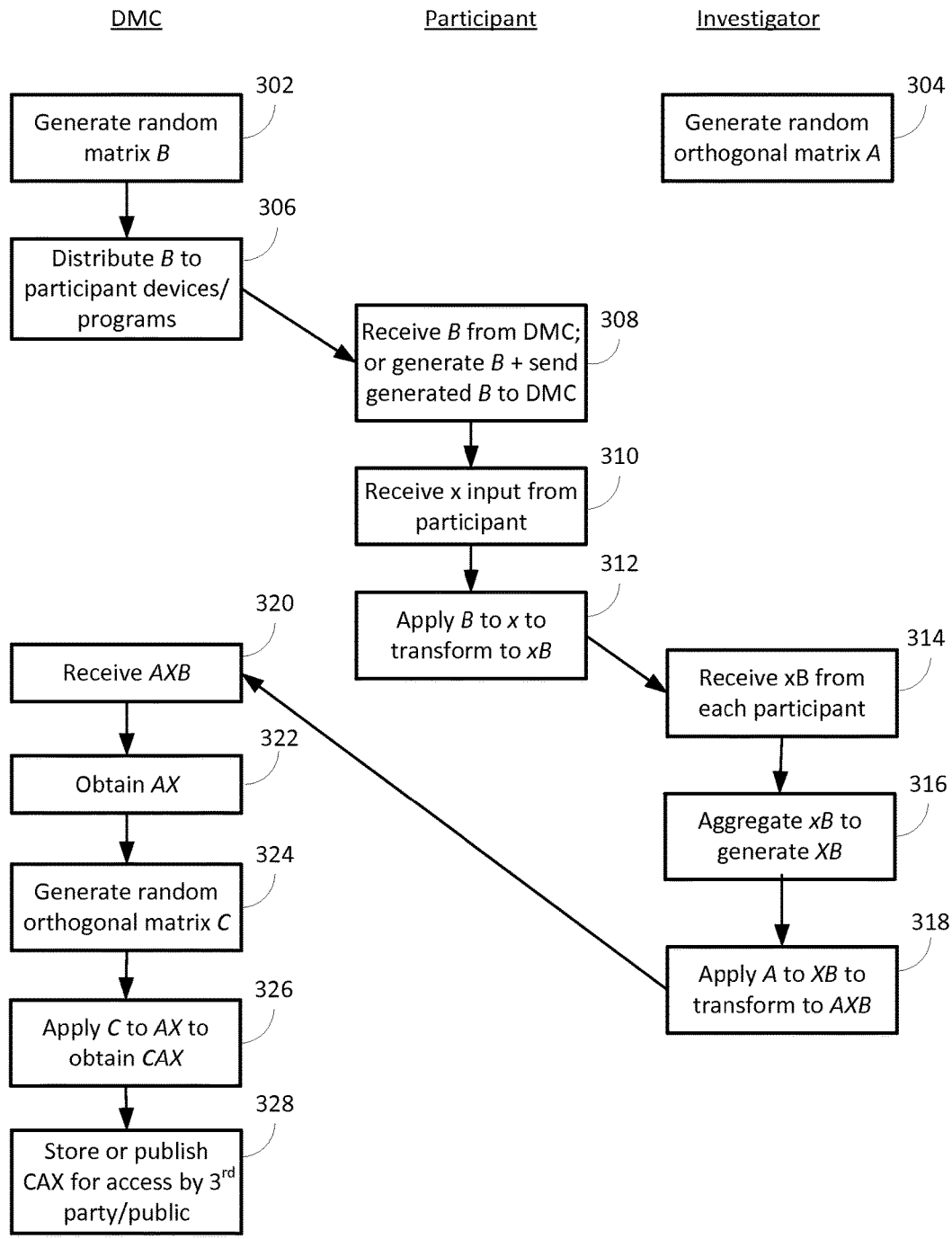
FIG. 3A illustrates a process flow of an example matrix masking technique.

FIG. 3A illustrates a process flow of an example masking technique. Referring to FIG. 3A, during the planning phase of a study, a Data Management Center (DMC)—or other data collector—can select a password which is used to generate a p×p random invertible matrix B (302). In some cases, the random invertible matrix B may be generated by accessing a server or service facilitating the data collection (and/or matrix masking). A trusted party (independent of the DMC) can select their own password (which will likely be different than that chosen by the DMC) to generate an n×n random orthogonal matrix A (304). The trusted party may also access (separately from the DMC) the server or service facilitating the data collection in order to generate the random orthogonal matrix A. The DMC's matrix B can be distributed by the DMC to the participants' data collection devices (306), while A is kept to the investigators. In operation 308, the participant device may receive the matrix B from the DMC (directly or via the server or service facilitating the data collection). In an alternative embodiment, the participant device (i.e., the program running on the participant device) may generate the matrix B, which would be provided by the participant device to the DMC (directly or via the server or service facilitating the data collection).

Random orthogonal matrices may be generated using the algorithm shown in FIG. 4 (illustrated as an implementation that can run in the Matlab® software from The MathWorks, Inc., but embodiments are not limited thereto). A Gram-Schmidt orthonormalization of a random matrix is used to generate a p by p orthogonal operator, which keeps the column vector of ones (1s) invariant. In the algorithm shown in FIG. 4, for a given vector size p and a seed value (or password), a random orthogonal matrix M of size p xp can be generated.

As data x (where x is a 1×p vector containing a single participant's sensitive information) is collected from participants' data collection devices (310), the data x is transformed as xB by applying the matrix B to x (312). Since the DMC would know B, the DMC does not receive XB. Instead, the trusted party receives xB from each participant (314). Individual participant's data are aggregated by (or on behalf of) the trusted party into XB (316), which is an n×p data matrix for a cohort of n participants. A "cohort" refers to a group of individuals that share a common characteristic.

A second transformation (using the random orthogonal matrix A) is applied to XB, resulting in a doubly masked data matrix AXB (318). The matrix AXB can be provided to the DMC (320). The DMC may control or oversee the data collection system. Analysts at the DMC can obtain AX (322) by multiplying AXB with the inverse of matrix B (since the DMC knows B). In a further implementation, analysts at the DMC can select another password to produce an n×n random orthogonal matrix C (324), for example using the algorithm shown in FIG. 4. The DMC device then left-multiplies AX by C to obtain CAX (326), and publishes CAX (328), so that others who request the data can have access to orthogonally-transformed data.

In an example implementation, at the time of data collection, x is immediately transformed by B before leaving the participant's device; only xB is sent to the investigators. The investigators aggregate patient data into XB, where B serves as a column operator that transforms data attributes (variables) in X. The trusted party then applies record transformation, and sends AXB to the DMC. For the data analysts, the DMC can multiply AXB by inverse of B to get back AX, which can be analyzed to obtain the same results as if X was used under either the general linear model or contingency table analysis.

To access the data sent to (and/or managed by) the DMC, the investigators (data analysts or other public) have access to CAX, but not AX, because otherwise they will be able to obtain the original data by A'AX=X. The analysts are left with record-transformed data (CAX), which preserves sufficient statistics for the general linear model and for contingency table analysis. The reason for right-multiplying the column operator B (when receiving input from a participant) is that this operation can be done one row of X at a time. That is, the masking operation can be done independently at each participant's device, allowing the collection of masked data one record at a time.

Figure 5A:
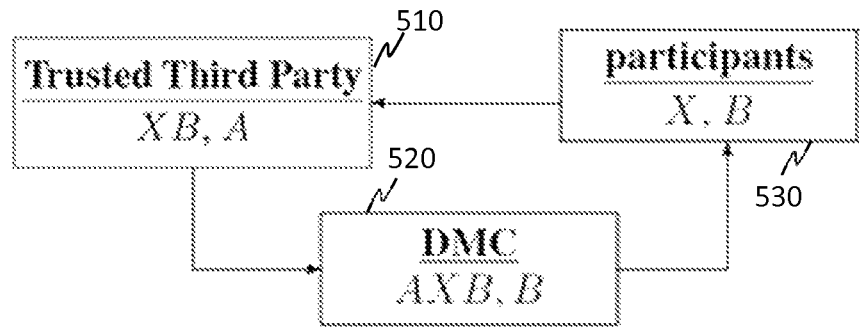
FIGS. 5A and 5B show diagrams indicating each entity's knowledge about data X and the matrix mask.
Figure 5B:
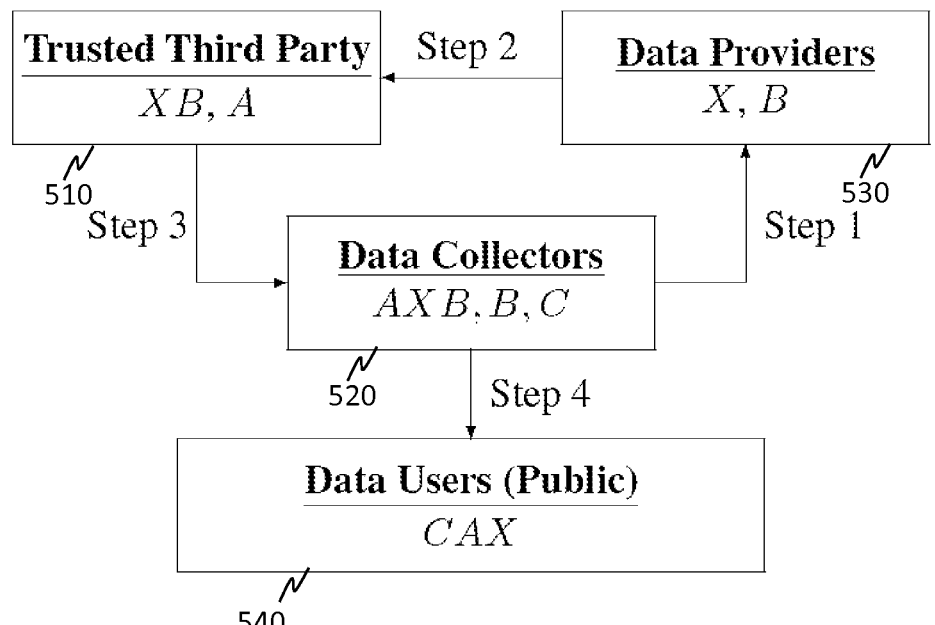

FIGS. 5A and 5B show diagrams indicating each entity's knowledge about data X and the matrix mask. Referring to FIG. 5A, the trusted third party 510 only knows XB, the DMC (or data collectors) 520 only know AXB and B (and therefore AX), and the participants (or other data providers) know X (or x). As further illustrated in FIG. 5B, other parties, such as data users (or the public) 540 may have access to the masked data, for example by the DMC (or data collectors) 520 publishing CAX. Only the participants 530 know the original data X (and only their own contribution x).

From another perspective, the trusted third party 510 may be a simple entity (or application) that does not perform any analysis with the collected data, but rather performs a function to further mask the data by applying the orthogonal matrix A before providing the participant data to the data collectors/data management center. Therefore, it should be understood that although the titles "data collectors," "data analyst," or "data manager" may be used or inferred as being the entities involved in the masking procedure, the actual entities and what they do with the data is not limited to the labels provided here. Instead, the procedure enables secure masking of the data for any party having access to the data and can be considered to have an associated level of permissions.

The security proof of the masking procedure is briefly given as follows: Let S be a set consisting of all data matrices that are orthogonal transformations of X, which are equivalent to orthogonal transformations of CAX. Because any member in S may result in the masked data (namely, CAX), following the procedure variously illustrated in FIGS. 3A, 4, 5A, and 5B, for data users (e.g., the public) who have access to CAX (and only know that A and C are random orthogonal matrices but do not know A and C), these data users only know that X belongs to the set S. That is, for any W=ΓX from S where Γ is an orthogonal matrix, there exist two orthogonal matrices $\bar{C}=C$ and $\bar{A}=A\Gamma'$ such that data users receive $\bar{C}\bar{A}W=CAX$. Similarly, the data collectors who have access to AX and CAX only know that the original data X is an element in S (because these data collectors may know C, but not A). Lastly, the trusted third party has access to XB in addition to CAX (the data available to the public), thus this party knows that each column vector of X belongs to the subspace spanned by the column vectors of XB and that X is an element in S. However, the trusted third party does not know B or C and does not have enough information to disclose values of data in X because B is a general invertible matrix.

Advantageously, because row operators A and C are orthogonal matrices, CAX preserves sufficient statistics for the general linear model and for contingency table analysis. In other words, CAX can be analyzed to obtain the same results as if X was used under either the general linear model or contingency table analysis. The main reason for right-multiplying the column operator B in the first step is that this operation can be done one row of X at a time. That is, the masking operation can be done independently at each participant's device, allowing the collection of masked data one record at a time.

As illustrated in FIG. 4, for the choice of orthogonal operator, both row (e.g., matrix A, matrix C) operators can be obtained by the Gram-Schmidt orthonormalization of a random matrix, which is controlled by some random number generator seeds (i.e., passwords). Where $M_1$ and $M_2$ are Gram-Schmidt orthonormalizations of $[1_n;Z_1]$ and $[1_n;Z_2]$, respectively, both $M_1$ and $M_2$ have the first column vector parallel to $1_n$, and $A=M_2M'_1$ transforms column vectors in $M_1$ to those in $M_2$. Therefore A is an orthogonal matrix that keeps $1_n$ invariant.

Several useful features, including a serial lock and quality assurance technique for the matrix masking procedure, can be easily implemented in the proposed privacy-preserving data collection and analysis system. One can inhibit the participants, the investigators, and the DMC from working together to recover the data matrix X with serial locks controlled by trusted third parties. Since the product of orthogonal matrices is an orthogonal matrix, the matrix A can be defined as a product of k orthogonal matrices: $A=\Pi_{i=1}^{k}A_i$, determined by a password (or key). Thus, in order to uncover the matrix A, all the passwords are needed. Specifically, the participants/data providers send XB to the first trusted third party, who applies $A_k$ and sends $A_kXB$ to the next third party; and the same process repeats until the kth third party sends $A=\Pi_{i=1}^{k}A_iXB$ to the data collectors/DMC. In other words, the security of the masking procedure can be assured because the original data X is compromised only when all trusted third parties are compromised. FIGS. 3C and 5E illustrate an example implementation incorporating a plurality of trusted third parties.

In case that the data X is no longer sensitive after certain time, the data can be retrieved with all passwords released by the investigators and the third parties. On the other hand, if there is no need to recover X in the future or it is necessary to keep X permanently masked, then the investigators and the third parties may choose to delete their passwords (or the passwords expire and scramble or disappear), which ensures that no one will be able to reconstruct all $A_i$, and hence no one can recover the original data X Another feature that may be implemented is a device that can be used to aid the data analysts or collectors in checking whether appropriate transformations using A and B were applied to the original data X To do so, the matrix X is used for adding the column of 1s (1n) as the first column, as well as a column of constants (say, c) as the last column. Then after the analysts reverse the B transformation to get AX, the last column of AX should be c times the first column of AX. Also, in the case that A is an orthogonal matrix that keeps 1n invariant, the last column of AX should equal to c $1_n$.

In many applications, clustering analysis and logistic regression may be performed on the attribute-transformed data (XB). The matrix masking procedure can be modified so that the DMC knows XB but no one except participants knows the original data X.

In certain applications, investigators may want to access part of the data (such as treatment group, demographic, and medical record), while keeping the sensitive information hidden. The above procedure can be modified to accomplish this task of partial masking. For example, the data set X can be separated into $X_1$ and $X_2$, where $X_1$ is for non-sensitive information and $X_2$ is for the sensitive information. More specifically, $X_1$ is an n×$p_1$ matrix for the non-sensitive data (for example, demographic and clinical data), and $X_2$ is an n $p_2$ matrix for sensitive information.

For this implementation it is assumed that the first column of both matrices is non-private pseudo-identifiers. The investigators have access to $X_1$ and $X_2B$, where the sensitive information is masked through attribute-transformation with B, but the first column is kept invariant to facilitate merging. The investigators send record-transformed data [$AX_1$, $AX_2B$] to the DMC. Data analysts in the DMC can recover [$AX_1,AX_2$] and analyze the transformed data as described earlier for either general linear model or contingency table analysis. Here, the investigators only know $X_2B$, the DMC only knows $AX_2$, and no one knows $X_2$.

As a further explanation, data collectors may choose B from block diagonal matrices with a $p_1 \times p_1$ identity matrix on the top left corner (i.e., $B=\text{diag}(I_{p_1}, B_2)$). Accordingly, the trusted third party can receive $XB=[X_1,X_2B_2]$, where the sensitive information is masked through attribute-transformation with $B_2$. In addition, the trusted third party and the data collectors generated orthogonal matrices A and C that keep $X_1$ invariant, which allows data users to have access to $X_1$ because $CAX=[X_1,CAX_2]$.

Although the example illustrated in FIG. 3A (and FIGS. 5A and 5B) shows the DMC having knowledge of matrix B and the third party having knowledge of matrix A, the usage of the two random matrices may be reversed (i.e., the DMC generates the row operator A and the third party applies the column operator B).

In certain implementations, an augmented data matrix may be utilized. For example, the data collection system may be programmed so that the original data x from each participant is independently augmented to x* with extra rows of random noise. The random noise may be applied at the participant's device or via some other method or system in a manner that retains the confidentiality of the data. When the DMC manages the data collection system, the noise may be applied in a manner that the DMC does not know the particular random noise.

Figure 3B:
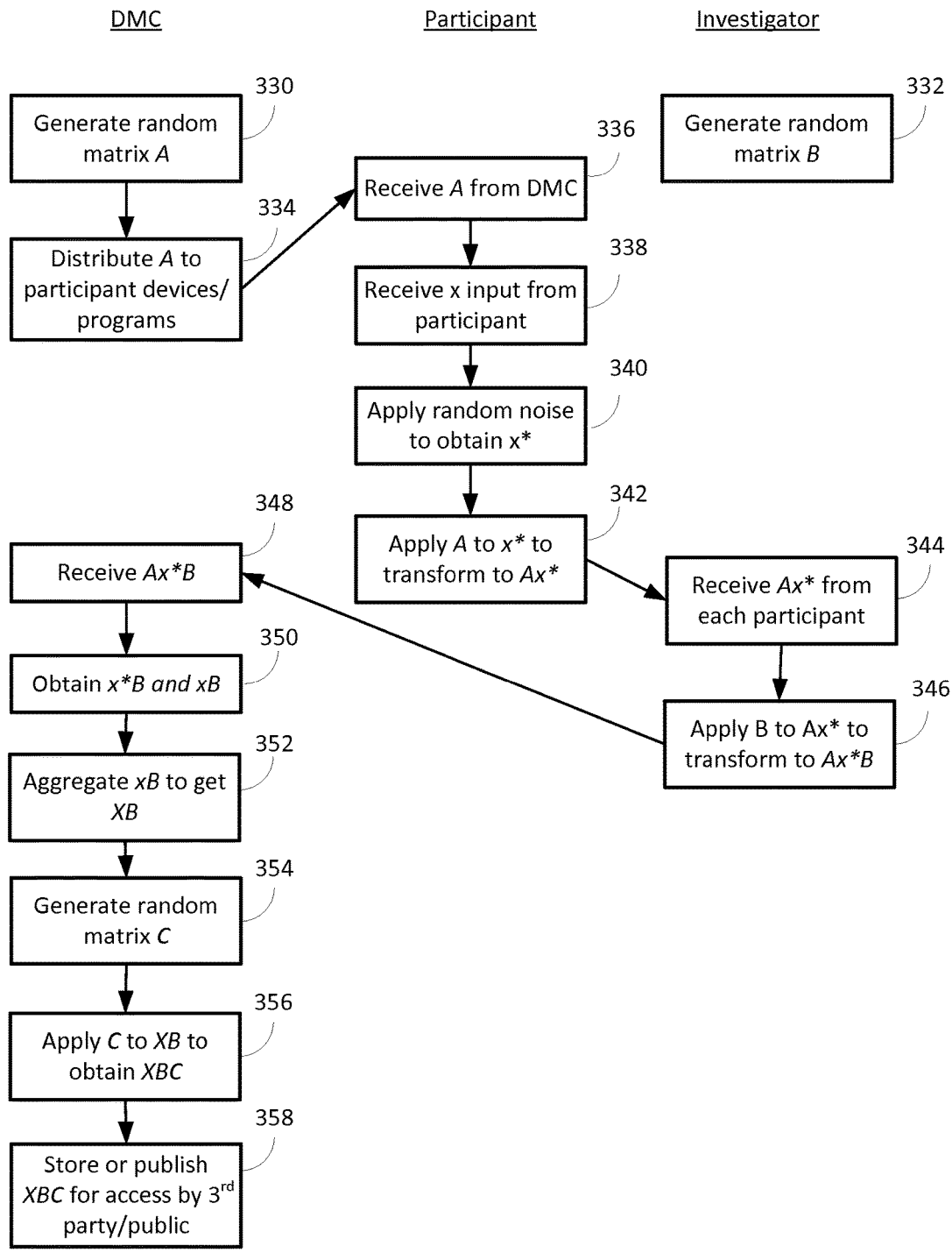
FIG. 3B illustrates a process flow of an example matrix masking technique in which an augmented data matrix is utilized.
Figure 3C:
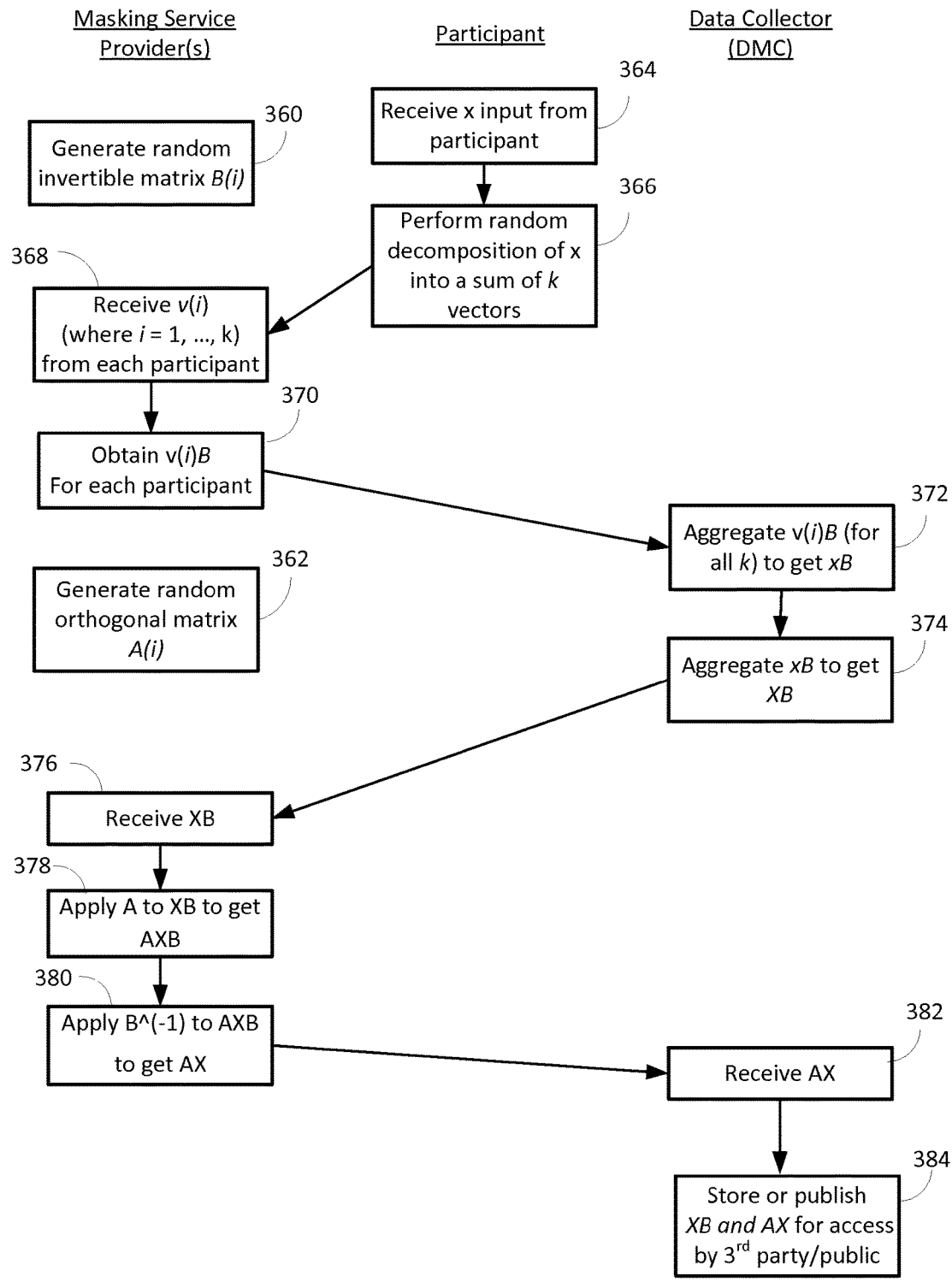
FIG. 3C illustrates a process for of an example matrix masking technique involving multiple masking service providers.

FIG. 3B illustrates a process flow of an example masking technique in which an augmented data matrix is utilized. For the implementation illustrated in FIG. 3B, the DMC may generate the matrix A (330) and the investigators may generate the matrix B (332). The DMC (or other data collectors) may plan the data collection, create a database structure, and instantiate a data collection system. A key may be selected to generate the r×r random invertible matrix A. As mentioned above, a service facilitating the data collection (and matrix masking) may be used by the DMC and/or investigators to generate appropriate matrices (and provide appropriate information and data to the proper parties).

Once the DMC generates the matrix A, the matrix A is provided to the participant device(s) (334). Data x input to the participant device can be received (338) and augmented by applying random noise to obtain x* (340). That is, at the time of data collection, a participant's data x can be independently augmented to x* with extra rows of random noise (which are not known by the data collectors). The matrix A (received by the participant device (336)) can be applied to x* to obtain Ax* (342). The transformed data Ax* is sent by the participant to the trusted party. The (r–1) extra rows provided as a result of the extra rows of random noise are included so that the left-multiplication of A can be performed.

After the trusted third party receives the transformed data Ax* (344), the trusted third party applies attribute-transformation (using the matrix B) (346) and sends Ax*B to the DMC (348). For example, the trusted party may select a key to generate the p×p random orthogonal matrix B.

Data analysts (or collectors) in the DMC left-multiply Ax*B by $A^{-1}$ to get back x*B (350). The first row of x*B is xB, and the data xB can be aggregated from participants to get XB (352).

Optionally, the data analysts may select another password to produce a p×p random matrix C (352). The DMC may then right-multiply XB by C to obtain XBC (356). XBC can then be published (358), so that others (including investigators) who request the data can have access to XBC.

Figure 5C:
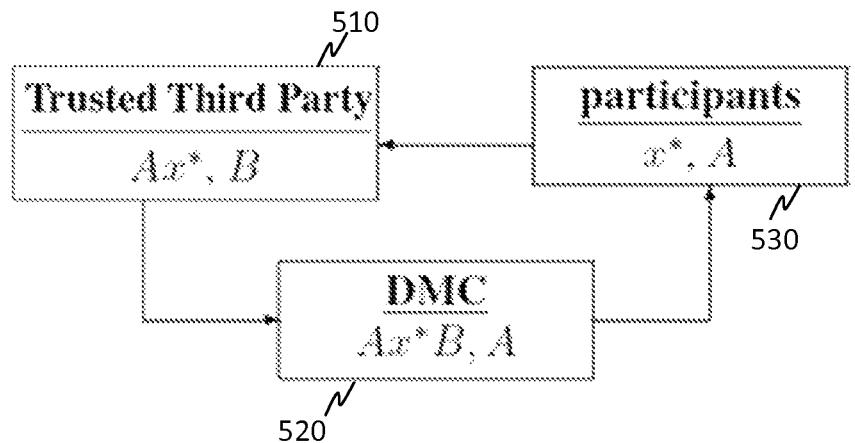
FIGS. 5C and 5D show diagrams indicating each entity's knowledge about an augmented data matrix x* and the matrix mask.
Figure 5D:
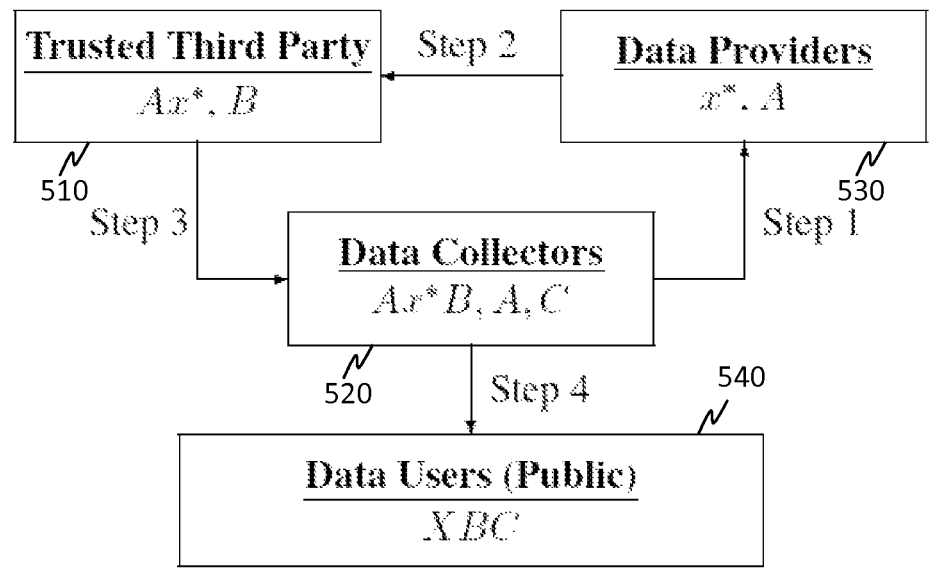

FIGS. 5C and 5D show diagrams indicating each entity's knowledge about an augmented data matrix x* and the matrix mask. Referring to FIG. 5C, the trusted third party 510 only know Ax* and the DMC (or data collectors) 520 only knows x*B (because of knowing A and receiving Ax*B from the trusted third party 510), where x* is an augmented data matrix with extra rows of random noise appended to record x provided by a participant 530. As further illustrated in FIG. 5D, other parties such as data users (or the public) 540 may have access to the masked data, for example by the DMC (or data collectors) 520 publishing XBC.

Similar to the masking procedure described above with respect to FIGS. 3A and 5A-5B, quality assurance can be conducted using a device for analysts to check whether an appropriate transformations were applied correctly to the augmented data x*. Here, a row of constants (c) is added as the last row among the extra rows of random noise appended to the original data x. In addition, a column operator B is selected that satisfies $1'_n B = 1_n'$, which can be generated by taking the transpose of an orthogonal matrix that keeps ln invariant. After the analysts remove the A transformation to obtain x*B, the last row of x*B should equal to a $cl'_n$.

When the column operator B is chosen such that variables corresponding to response and treatment groups are invariant, then the same results for the treatment effects can be obtained from the masked data XBC using logistic regression. However, the effects of other covariates cannot be estimated based on the above masking procedure.

Because logistic regression is one of the most widely used statistical methods in biomedical and social research, many people have investigated approaches to conduct privacy preserved logistic regression with multiple sources. Advantageously, treatment effects can be analyzed while maintaining data private—even during collection—because matrix masking is performed when each participant's data is collected and nobody except the participant knows actual covariate values. This is in contrast to other approaches that begin with participants' unmasked data before conducting the privacy preserved logistic regression.

According to various embodiments of the invention, matrix masking is performed at the time of data collection. The procedure lets the investigative team and the analyst team each hold a key for the generation of a random operator. Both operators are applied to mask the data. Neither investigators nor analysts see the original data, but standard statistical analysis can still be performed with the same results for masked data as for the original data. Therefore, confidentiality of the data and privacy of participants are fully protected. In addition, an error checking mechanism is built in the data collection procedure to make sure that the data used for analysis are indeed an orthogonal transformation of the original data. With the ever growing amount of data generated by electronic devices and the increasing demand for privacy protection, the method can be a great tool for survey research or clinical studies.

FIG. 3C illustrates a process flow of an example masking technique involving multiple masking service providers. For the implementation illustrated in FIG. 3C, the matrices A and B are each generated in plurality and held by corresponding ones of masking service providers. The masking service providers may be part of a service facilitating the matrix masking For example, a server hosting the service may also manage a plurality of resources (virtual and/or physical) that provide a plurality of independent masking service providers. Through the service, each masking service provider generates a random invertible matrix B(i) (360) and a random orthogonal matrix A(i) (362), where $1 \leq i \leq k$ (and i and k are integers and k represents the number of components into which a participant's data is decomposed).

The data collection system can be designed such that each masking service provider generates an n×n random orthogonal matrix for left multiplying masking (A) and a p×p random invertible matrix for right multiplying masking (B), where the matrices for right-multiplying masking (B) commute in product order. The matrices A and B may be generated before or after collection of data begins.

Data x input to the participant device can be received (364) and randomly decomposed into a sum of k vectors (366). That is, at the time of data collection, a participant's data x (1×p vector containing a single participant's sensitive information) is randomly decomposed into a sum of k vectors: $x = v_1 + v_2 + \ldots v_k$. In a specific implementation, the jth element of $v_i$ equals $w_{ij}x_j$, where $w = (w_{ij}, 1 \leq i \leq k, \leq j \leq p)$ is a random weight matrix.

The masking service provider(s) receive the decomposed data (368). The i-th component of decomposed data ($v_i$) is first sent to the i-th trusted third party (of the masking service providers) to right multiply $v_i$ by Bi and then sent to all other third parties (masking service providers) for matrix masking as $v_iB$ (370), where $B = \Pi_{i=1}^{k} B_i$ is the product of all right multiplying matrices (note that the k matrices are commuting in product and the order of multiplication does not matter). Here, attributes transformations can be carried out by sequentially right-multiplying k invertible matrices (Bi) for each component of the decomposed data. The masked data component $v_iB$ is sent to the DMC (data collectors), which aggregates all the masked data components in order to get the transformed data xB (372). That is, all the masked components $v_iB$, $1 \leq i \leq k$ are added together to obtain xB.

After receiving data from all third participants, the data collector(s) aggregate the individual data into X B (374), which is sent back to trusted third parties (the masking service providers) to remove the right multiplying masking B and add left multiplying masking A.

After the trusted third party (the service and/or masking service providers) receives the transformed data XB (376), the service left multiplies by Ai (378) in sequence to get AXB, where $A = \Pi_{i=1}^{k} A_i$. Next, the trusted third parties right-multiply the masked data AX B by $Bi^{-1}$ in sequence to remove B and get AX (380). With the receipt of AX (382), the data collectors may publish both XB and AX for access by data users (384).

FIG. 5E shows a diagram indicating each entity's knowledge about data for an implementation with a masking service provider. Referring to FIG. 5E, as the trusted third party/parties, a masking service provider 550 can include a plurality of masking service providers where an i-th masking service provider generates a column operator Bi and a row operator Ai, and knows a component of decomposed data vi and data masked by other third parties $\bar{v}_{(i)}$. The data collectors 520 know masked data $v_iB$ in addition to AX and XB, which are available to anyone including the public 540. No one other than data providers 530 (participating patients and doctors) know the original data x since only the vector components are separately known by the masking service providers(s) 550.

The following examples are presented to provide a greater understanding of certain embodiments of the present invention and of some of its many advantages. The following examples are simply meant to be illustrative of some of the applications and variants for embodiments of the invention. They are, of course, not to be considered in any way limitative of the invention.

EXAMPLE

TMM-1 and TMM-2

Two matrix masking procedures (Example TMM-1 and Example TMM-2) are illustrated using a random subset of 20 observations from the LEAPS study described by Duncan, P. W., Sullivan, K. J., Behrman, A. L., Azen, S. P., Wu, S. S., Nadeau, S. E., Dobkin, B. H., Rose, D. K., Tilson, J. K., Cen, S., Hayden, S. K., for The LEAPS Investigative Team, "Body-weight-supported treadmill rehabilitation after stroke," New England Journal of Medicine 364(21), 2026-2036, (2011). A brief description of the eight variables about the original data from the LEAPS study is shown in Table 1 of FIG. 6 and the random subset of 20 observations from LEAPS (the original data matrix X) is shown in Table 2 of FIG. 7.

Even though the collected data is not extremely sensitive, if this data was collected based on GPS signals using a smartphone, the location information can be considered to be sensitive data. The examples provided here illustrate how the sensitive information can be masked and the data used for relevant analysis.

TMM-1

In a first step, the data collection is planned. This may be accomplished by the data collectors creating a database for structured data including Subject ID, the eight variables shown in FIG. 6, and a variable for quality assurance. A web-based data entry system can be implemented for each participant to enter the data. For the example, a key of 535 is selected as the random seed to generate a 9×9 random invertible matrix B, which is incorporated to the data entry system.

In a second step, at the time of data collection, each participant can enter data. For example, for the first participant, the data may be as shown in the first row of Table 2 of FIG. 7. Once the participant enters the data, the record can be immediately transformed by B and only the masked data remains (e.g., would be stored) as shown in Table 3 of FIG. 8. The masked data may be stored upon transmittal to a trusted third party (not the data collectors).

In a third step, the trusted third party can select a key, for example a key of 536, and generate a 20×20 random orthogonal matrix A. This may be accomplished using the Matlab® program illustrated in FIG. 4 with A=GenerateROM(536, 20). After receiving the attribute-transformed data from all participants (XB such as shown in Table 3 of FIG. 8), the trusted third party applies record transformation and sends the doubly masked data (AXB shown in Table 4 of FIG. 9) to the data collectors.

In a fourth step, the data collectors multiply AXB received from the trusted third party with $B^{-1}$ (since the data collectors know B) to get back AX. Then, the data collectors can select another key, 537 in this example, to produce a 20×20 random orthogonal matrix C. This may be accomplished using the Matlab® program illustrated in FIG. 4 with C=GenerateROM(537, 20). Using C, the data collectors can left-multiply AX by C and then publish the masked data CAX such as shown in Table 5 of FIG. 10 so that data users can have access to orthogonally-transformed data.

Figure 11B:
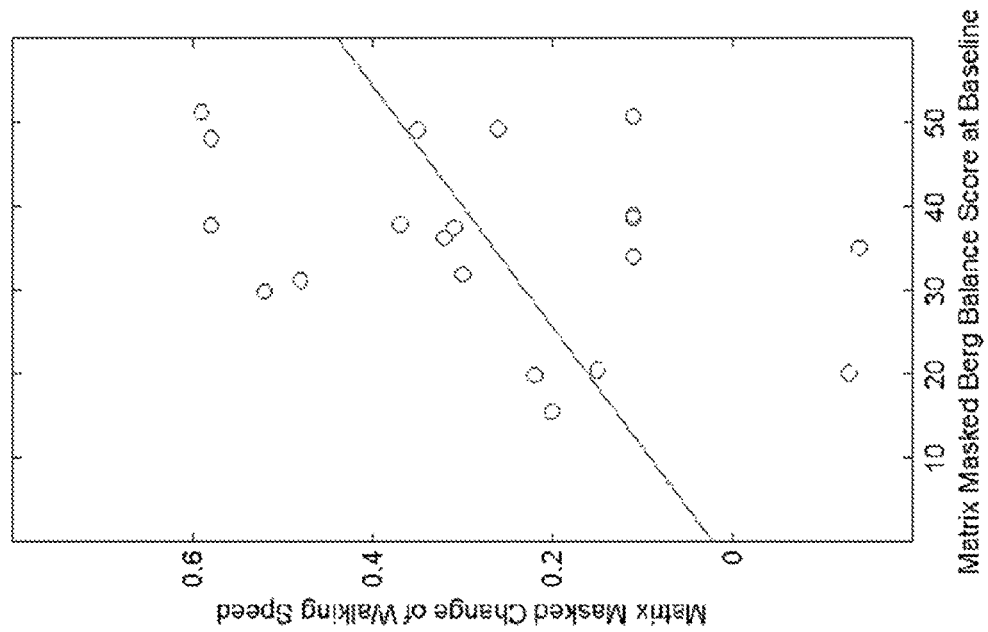
FIGS. 11A and 11B show scatter plots and fitted least-squares lines for the original and matrix masked data.
Figure 11A:
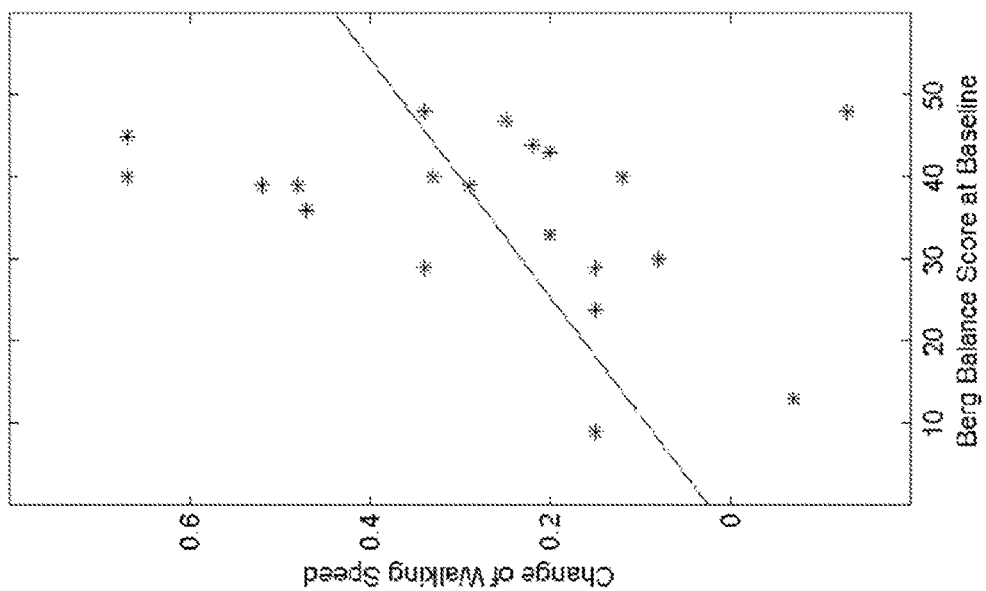

Accordingly, Tables 3-5 of FIGS. 8-10 show the matrix masked data XB, AXB and CAX, respectively. FIGS. 11A and 11B show scatter plots and fitted least-squares lines for the original and matrix masked data. FIG. 11A is the actual data and its model fit and FIG. 11B is the masked data and its model fit. As shown by comparing FIGS. 11A and 11B, the points in the matrix masked data have been completely scrambled and bear no relationship with the original data points; yet the regression line is the same for the actual data and masked data and the residuals from both regressions would have the same distribution if they are normally distributed.

In some cases, the fourth step may be modified to allow data users to perform different types of statistical analysis. For example, once the data collectors recover AX, they can produce an orthogonal matrix $\Gamma_1$ and send $AX\Gamma_1$ back to the trusted third party, who removes A and returns $X\Gamma_1\Gamma_2$. This allows data users to access both CAX and $X\Gamma_1\Gamma_2$, where C and A are orthogonal while $\Gamma_1$ and $\Gamma_2$ are general invertible matrices.

TMM-2

Using the 1st and 11th observations ("participant") of the random subset of 20 observations from LEAPS shown in Table 2 of FIG. 7, an augmented matrix can be generated.

For example, in a first step, data collectors may plan a data collection similar to the first step in the Example TMM-1 approach above, except that there is no variable for quality assurance. Instead, a key, for example 535, is selected as a random seed to generate an 8×8 random invertible matrix A.

In a second step, at data collection, six rows of normal random noise and a row of quality assurance data can be added to each participant's data (see Table 6 of FIG. 12). The record is immediately masked and only the transformed data (Ax* shown in Table 7 of FIG. 13) is sent to the trusted third party and saved in the database. The trusted third party may collect the data from each participant separately.

In a third step, the trusted third party can select a column operator B, which is constructed to be block diagonal so that it keeps the first three columns invariant with the lower 6×6 block being transpose of the matrix generated by GenerateROM(536, 6) as provided in the algorithm of FIG. 4. The trusted third party can apply the attribute-transformation B, and send the doubly masked data Ax*B (such as shown in Table 8 of FIG. 14) to the data collectors.

In a fourth step, the data collectors left-multiply Ax*B by $A^{-1}$ (since the data collectors know A) to get back x*B. The data collectors can then extract the first row of x*B to get xB and aggregate the data xB from the participants to generate XB. The data collectors can then select another key, for example 537, and produce random orthogonal matrix C, which has the same diagonal structure as B but the lower 6×6 block is the transpose of the matrix generated by GenerateROM(537, 6) as provided in the algorithm of FIG. 4. The data collectors can then right-multiply XB by C and publish XBC such as shown in Table 9 of FIG. 15 so that data users can have access to the orthogonally-transformed data.

Accordingly, Tables 7-9 of FIGS. 13-15 show the two selected observations of matrix masked data AX*, AX*B and XBC, respectively.

In some cases, the fourth step may be modified to allow data users to perform different types of statistical analysis. For example, once the data collectors recover XB, they can produce an orthogonal matrix $\Gamma_1$ and sends $\Gamma_1 XB$ back to the trusted third party, who removes B and returns $\Gamma_2 \Gamma_1 X$.

Then, with C being a general invertible matrix, the data collectors release $\Gamma_2 \Gamma_1 X$ and XBC to data users, who can conduct general linear regression, contingency table analysis or logistic regression.

EXAMPLE

Illustrating Preservation of Statistics for Analysis

Orthogonal transformation of data preserves sufficient statistics for enabling analysis of confidential data while the underlying data remains confidential. For example, consider the general linear model, $$Y = X\beta + \varepsilon;$$

where $Y_{n\times 1}$ is the vector for the outcome variable, $X_{n\times p}$ is the model matrix, $\beta_{p\times 1}$ is the vector of unknown parameters, and $\varepsilon_{n\times 1}$ is the vector of zero-mean random error terms (usually also assumed to be normally distributed). The usual least-squares estimate $\hat{\beta}$ is the vector which minimizes the sum of squared errors $\|Y-X\beta\|_2^2$; it is also the maximum likelihood estimate (MLE) when $\varepsilon$ is normal. When matrix X is of full rank, the expression for the estimate $\hat{\beta}$, which is the unique minimizer of the sum of squared errors is $\hat{\beta}=(X'X)^{-1}X'Y$, where apostrophe (') denotes transpose.

An orthogonal transformation is applied to the outcome vector $Y_{n\times 1}$, and the same orthogonal transformation is applied to the model matrix $X_{n\times p}$. An orthogonal transformation is a mapping from $R^n$ to $R^n$ that preserves lengths of vectors and angles between vectors. The orthogonal transformation may be represented by a square matrix $A_{n\times n}$ such that A'A=I, where I is the identity matrix. The model is then fit based on AY and AX rather than the original model based on Y and X. That is, $AY=AX\beta_{new}+A\varepsilon$, where $A\varepsilon$ remains a zero-mean vector. A is a row operator that transforms data records in X, where each row (or record) represents one case. The original least-squares estimate is denoted as $\hat{\beta}_{orig}$, and the new least-squares estimate on orthogonally-transformed data is denoted as $\hat{\beta}_{new}$. Then, $\hat{\beta}_{new}=((AX)'(AX))^{-1}(AX)'(AY)=(X'X)^{-1}(X'Y)=\hat{\beta}_{orig}$.

In other words, the least-squares estimates from the original and transformed data are the same when left-multiplying the data by an orthogonal matrix. This result can be confirmed by considering the usual geometric representation of the least-squares estimate. Stated in terms of the original estimate, the geometric interpretation is that $\hat{\beta}_{orig}$ provides a linear combination of the column vectors in X such that the distance between the vector Y and the vector of predicted values $X\hat{\beta}$ is the shortest, among all vectors in the subspace spanned by the column vectors of X. Since orthogonal transformations preserve distances and angles between vectors, $\hat{\beta}_{new}=\hat{\beta}_{orig}$ and the regression parameter estimates are identical for the two models even if only a subset of variables from X (and the corresponding subset from AX) is used.

The residual vector for the original data is defined to be $e=Y-X\hat{\beta}$. For the new data, the residual vector is $AY-AX\hat{\beta}=A(Y-X\hat{\beta})=Ae$, which is the original residuals transformed by A. Since length is preserved by orthogonal transformation, the residual sum of squares will be the same for the two models. Furthermore, because the covariance of $\hat{\beta}$ only depends on the residual sum of squares and on $X'X=(AX)'(AX)$, the estimate of the covariance matrix as well as all inference procedures will be identical. However, the individual residuals will be transformed so that residual plots and diagnostic methods will no longer be valid.

When an intercept term is included in a regression analysis, $1_n$ is a column of X, where $1_n$ denotes the vector of n 1's. In this case, $A1_n$ is a column of AX Therefore, the first and second moment of X can be derived from AX. On the other hand, if A is restricted to be an orthogonal matrix that keeps $1_n$ invariant (i.e., $A1_n=1_n$), then the sample means and sample covariance matrix for X and AX are the same.

Count data can be analyzed by contingency table methods. In particular, suppose $x_1$ and $x_2$ are two length-n binary (0-1) variables. The data are commonly summarized as counts in a 2×2 table as shown in Table 10 of FIG. 16, with rows labeled by the values of variable $x_1$ and columns labeled by the values of variable $x_2$.

Now $x'_1 x_1 = c+d$ is the number of 1's in vector $x_1$, $x'_2 x_2 = b+d$ is the number of 1's in vector $x_2$, and $x'_1 x_2 = d$ is the number of 1's that $x_1$ and $x_2$ have in common. Knowledge of these three values in the table (one row total, one column total, and one cell), as well as sample size n, is sufficient to fill in the whole table (e.g., a, b, c, and d). Next, it can be observed that the data can be transformed by an orthogonal matrix and the same results can be obtained from statistical analysis as from the original data. More specifically, to hide $x_1$ and $x_2$, both $x_1$ and $x_2$ can be multiplied by orthogonal matrix A. Note that $(Ax_1)'(Ax_1)=x'_1 x_1$, $(Ax_2)'(Ax_2)=x'_2 x_2$, and $(Ax_1)'(Ax_2)=x'_1 x_2$. Thus, the same counts are obtained for the three quantities considered previously, as if they were obtained with the original data. Since these three counts are sufficient for the whole table, the whole table will be identical for the orthogonally-transformed data as for the original data. Therefore, the usual analysis, including the chi-squared test and estimation of relative risk and odds ratio, will yield identical results for the transformed data as for the original data.

For variables with multiple levels, the contingency table remains invariant if dummy binary indicator variables are included. If data analysts have access to the attribute-transformed data (XB), then cluster analysis and logistic regression can be conducted on transformed data with the same results as the original data. Because orthogonal transformation does not change the Euclidean distances between records, it is possible to obtain exactly the same results for distance-based clustering. For a binary logistic regression model $logit[\pi(X)]=X\beta$, one usually estimates parameter $\beta$ by a method of maximum likelihood and conducts statistical inference based on general asymptotic results, i.e., estimating the covariance matrix by $\widehat{Cov}(\hat{\beta})=\{X'Diag[\hat{\pi}_i(1-\hat{\pi}_i)]X\}^{-1}$; where $Diag[\hat{\pi}_i(1-\hat{\pi}_i)]$ is a diagonal matrix with elements $\hat{\pi}_i(1-\hat{\pi}_i)$ on the main diagonal and $\hat{\pi}_i$ denotes the maximum likelihood estimate of the response probability for the ith subject. A column operator B can be selected such that variables corresponding to response and treatment groups are invariant, and the column transformation is only applied to covariates, i.e., B is a block diagonal matrix with an identity matrix on the top left corresponding to response and dummy variables of treatment effects. In this case, it is possible to show that the maximum likelihood estimate of the treatment effects and their corresponding estimated standard errors are the same for the original data and the matrix-masked data.

EXAMPLE

Computing System

A computing system for performing triple matrix masking can include a processor and storage system in which one or more applications may be loaded.

The processor may include a microprocessor and other circuitry that retrieves and executes software (including applications and/or an operating system) from the storage system. The processor may be implemented within a single processing device but may also be distributed across multiple processing devices or sub-systems that cooperate in executing program instructions. Examples of a processor include general purpose central processing units, application specific processors, and logic devices, as well as any other type of processing device, combinations, or variations thereof.

The storage system can store software as well as data generated during the execution of the software. The storage system may comprise any computer readable storage media readable by processor and capable of storing software.

Carrier waves and other propagating signals that may contain data usable by a computer system are not themselves "storage media." That is, "computer-readable storage media" and "storage media" do not consist of carrier waves or propagating signals.

Storage system may include volatile and nonvolatile, removable and non-removable media implemented in any method or technology for storage of information, such as computer readable instructions, data structures, program modules, or other data. For example, non-volatile storage may be available within the storage system to store persistent information that should not be lost if the system is powered down.

Examples of storage media include random access memory (including RAM, DRAM, DDR SDRAM, SRAM); read only memory (ROM, PROM, EPROM, EEPROM); flash memory (NVRAM); magnetic and ferromagnetic/ferroelectric memories (MRAM, FeRAM); resistive memories and memristors (resistive random-access memory (Re-RAM), PCM, CBRAM); magnetic disks; optical disks; virtual memory and non-virtual memory, magnetic cassettes, magnetic tape, magnetic disk storage or other magnetic storage devices, or any other suitable storage media. In no case is the storage media a propagated signal.

In addition to storage media, in some implementations, storage system may also include communication media over which software may be communicated internally or externally. Storage system may be implemented as a single storage device but may also be implemented across multiple storage devices or sub-systems co-located or distributed relative to each other. Storage system may include additional elements, such as a controller, capable of communicating with processor.

The software may include additional processes, programs, or components. Software may also comprise firmware or some other form of machine-readable processing instructions executable by processor.

In general, software may, when loaded into the processor and executed, transform computing system overall from a general-purpose computing system into a special-purpose computing system. Indeed, encoding software on storage system may transform the physical structure of storage system. The specific transformation of the physical structure may depend on various factors in different implementations of this description. Examples of such factors may include, but are not limited to the technology used to implement the storage media of storage system and whether the computer-storage media are characterized as primary or secondary storage.

For example, if the computer-storage media are implemented as semiconductor-based memory, software may transform the physical state of the semiconductor memory when the program is encoded therein, such as by transforming the state of transistors, capacitors, or other discrete circuit elements constituting the semiconductor memory. A similar transformation may occur with respect to magnetic or optical media. Other transformations of physical media are possible without departing from the scope of the present description, with the foregoing examples provided only to facilitate this discussion.

Certain techniques set forth herein may be described in the general context of computer-executable instructions, such as program modules, executed by one or more computing devices. Generally, program modules include routines, programs, objects, components, and data structures that perform particular tasks or implement particular abstract data types.

Embodiments of the mask applications and mask algorithms may be implemented as a computer process, a computing system, or as an article of manufacture, such as a computer program product or computer-readable medium. Certain methods and processes described herein can be embodied as code and/or data, which may be stored on one or more computer-readable media. Certain embodiments of the invention contemplate the use of a machine in the form of a computer system within which a set of instructions, when executed, can cause the system to perform any one or more of the methodologies discussed above. Certain computer program products may be one or more computer-readable storage media readable by a computer system and encoding a computer program of instructions for executing a computer process.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A computer-implemented method for preserving privacy and masking personally identifiable information of a participant of a research study from a researcher, the method comprising:
   receiving, by a masking service provider device, unmasked data input from a participant electronic device of the participant of the research study;
   storing the unmasked data in a computer memory of the masked service provider device;
   before the data is available to a party other than the participant, transforming the data input from the participant to masked data by applying, by the masking service provider device, a first invertible matrix to the data input from the participant;
   aggregating the masked data of a plurality of participants to generate an aggregated data matrix;
   transforming the aggregated data matrix to a doubly masked matrix by applying an orthogonal matrix to the aggregated data matrix;
   obtaining a second masked data for analysis by removing the first matrix application from the doubly masked matrix; and
   transmitting the masked data to the researcher, thereby preserving the privacy and masking personally identifiable information of the participant of the research study.

2. The method of claim 1, further comprising generating the orthogonal matrix by performing a Gram-Schmidt orthonormalization of a random matrix.

3. The method of claim 1, further comprising:
   transforming the second masked data to a third masked data by applying a second orthogonal matrix to the second masked data; and
   publishing the third masked data.

4. The method of claim 3, further comprising generating the second orthogonal matrix by performing a Gram-Schmidt orthonormalization of a random matrix.

5. The method of claim 1, further comprising applying at least one additional row of random noise before transforming the data input from the participant electronic device to the masked data.

6. The method of claim 5, further comprising:
   transforming the masked data to a doubly masked matrix by applying a block diagonal matrix including a transpose of a second orthogonal matrix to the masked data.

7. The method of claim 6, further comprising generating the second orthogonal matrix by performing a Gram-Schmidt orthonormalization of a random matrix.

8. A computer-implemented method for preserving privacy and making personally identifiable information of a participant of a research study from a researcher, the method comprising:
   receiving, by a masking service provider device, unmasked data input from a participant electronic device of the participant of the research study;
   storing the unmasked data in a computer memory of the masked service provider device;
   before the data is available to a party other than the participant, transforming the data input from the participant to masked data by applying, by the masking service provider device, a first invertible matrix to the data input from the participant:
   obtaining a second masked data by removing the first invertible matrix application from the doubly masked matrix;
   removing the random noise by selecting a first row of the second masked data;
   aggregating the first row of the second masked data of a plurality of participants to generate an aggregated data matrix; and
   transmitting the masked data to the researcher, thereby preserving the privacy and masking personally identifiable information of the participant of the research study.

9. The method of claim 8, further comprising:
   transforming the aggregated data matrix to a third masked data by applying a third matrix comprising a third orthogonal matrix to the aggregated data matrix; and
   publishing the third masked data.

10. The method of claim 9, further comprising generating the third orthogonal matrix by performing a Gram-Schmidt orthonormalization of a random matrix.

11. The method of claim 1,
wherein, as data x is collected at the participant electronic device, x is immediately transformed by B to obtain xB before the data x leaves the participant electronic device,
wherein individual data is aggregated into XB, where B serves as a column operator that transforms data attributes in X,
wherein record transformation is applied by transforming XB by A to obtain AXB, and
wherein transmitting the masked data to the researcher comprises making the data available to the researcher in a form of AX or CAX, where A, B, and C are each random invertible matrices and at least one is a random orthogonal matrix.

12. The method of claim 1, wherein the participant electronic device data x is randomly decomposed into a sum of k vectors, and
wherein the k vectors are provided, as individual components of decomposed data, to the masking provider device.

13. A computer-implemented method for preserving privacy and masking personally identifiable information of a participant of a research study from a researcher, the method comprising:
receiving, by a masking service provider device unmasked data input from a participant electronic device of the participant of the research study;
storing the unmasked data in a computer memory of the masked service provider device;
before the data is available to a party other than the participant, transforming the data input from the participant to masked data by applying, by the masking service provider device, a first invertible matrix to the data input from the participant;
wherein the participant electronic device data x is randomly decomposed into a sum of k vectors,
wherein the k vectors are provided, as individual components of decomposed data to the masking provider device, and
wherein the method further comprises:
sequentially right-multiplying k invertible matrices for each individual component of the decomposed data to obtain a masked component; and
transmitting the masked data to the researcher, thereby preserving the privacy and masking personally identifiable information of the participant of the research study.

14. The method of claim 13, further comprising:
aggregating all the masked components into xB, where B is the product of the k invertible matrices, where the k invertible matrices are commuting in product; and
aggregating individual data into XB.

15. The method of claim 14, further comprising:
applying record transformations by transforming XB to AXB, where A is a product of k orthogonal matrices; and
publishing AX and XB.

16. A non-transitory computer-readable storage medium having stored thereon instructions for performing the method according to claim 1.

17. A system for preserving privacy and masking personally identifiable information of a participant of a research study from a researcher, the system comprising:
one or more non-transitory computer-readable storage media having instructions stored thereon that, when executed by a processing system, direct the processing system to:
generate k invertible matrices;
generate k orthogonal matrices;
provide one of the k invertible matrices to a corresponding a first masking service provider device of k masking service provider devices;
store the invertible in a computer memory of the first masked service provider device;
direct individual components of a total of k components from a randomly decomposed participant data to the k masking service provider devices to sequentially right-multiply the k invertible matrices to obtain a masked component for each of the k components;
provide the k masked components for aggregation into xB, where B is the product of the k invertible matrices;
receive aggregated individuals' data XB;
transform XB into AX, where A is a product of the k orthogonal matrices; and
transmit AX to the researcher, thereby preserving the privacy and masking personally identifiable information of the participant of the research study.

18. The system of claim 17, wherein the instructions that direct the processing system to generate the k orthogonal matrices comprise instructions to perform a Gram-Schmidt orthonormalization of a random matrix.

* * * * *

UNITED STATES PATENT AND TRADEMARK OFFICE
CERTIFICATE OF CORRECTION

PATENT NO. : 10,013,569 B2
APPLICATION NO. : 15/029512
DATED : July 3, 2018
INVENTOR(S) : Wu et al.

Page 1 of 1

It is certified that error appears in the above-identified patent and that said Letters Patent is hereby corrected as shown below:

In the Claims

Column 20,
Line 33, "participant data" should read --participant's data--.

Signed and Sealed this
Twenty-fifth Day of September, 2018

Andrei Iancu
*Director of the United States Patent and Trademark Office*